(12) United States Patent
Allum et al.

(10) Patent No.: US 8,677,999 B2
(45) Date of Patent: Mar. 25, 2014

(54) METHODS AND DEVICES FOR PROVIDING MECHANICAL VENTILATION WITH AN OPEN AIRWAY INTERFACE

(75) Inventors: Todd A. Allum, Livermore, CA (US); Anthony D. Wondka, Thousand Oaks, CA (US); Joseph Cipollone, Mission Viejo, CA (US); Lutz Freitag, Hemer (DE)

(73) Assignee: Breathe Technologies, Inc., Irvine, CA (US)

( * ) Notice: Subject to any disclaimer, the term of this patent is extended or adjusted under 35 U.S.C. 154(b) by 951 days.

(21) Appl. No.: 12/545,708

(22) Filed: Aug. 21, 2009

(65) Prior Publication Data

US 2010/0071693 A1 Mar. 25, 2010

Related U.S. Application Data

(60) Provisional application No. 61/091,198, filed on Aug. 22, 2008, provisional application No. 61/136,269, filed on Aug. 22, 2008.

(51) Int. Cl.
*A61M 16/00* (2006.01)
*A62B 7/00* (2006.01)
*A62B 9/00* (2006.01)
*A62B 9/04* (2006.01)

(52) U.S. Cl.
USPC ............. 128/204.25; 128/204.18; 128/202.27

(58) Field of Classification Search
USPC ............. 128/200.14, 200.18–200.22, 202.27, 128/203.12, 203.22, 203.25–203.26, 128/204.18, 204.24–204.25, 204.29, 128/205.11, 205.25, 207.14, 207.18, 911, 128/912
See application file for complete search history.

(56) References Cited

U.S. PATENT DOCUMENTS

| | | | |
|---|---|---|---|
| 50,641 | A | 10/1865 | Stone |
| 428,592 | A | 5/1890 | Chapman |
| 697,181 | A | 4/1902 | Smith |

(Continued)

FOREIGN PATENT DOCUMENTS

| | | |
|---|---|---|
| DE | 19626924 | 1/1998 |
| DE | 29902267 U1 | 7/1999 |

(Continued)

OTHER PUBLICATIONS

In the U.S. Patent and Trademark Office, Supplemental Notice of Allowance dated in re: U.S. Appl. No. 10/771,803, dated Dec. 2, 2008, 2 pages.

(Continued)

*Primary Examiner* — Oren Ginsberg
(74) *Attorney, Agent, or Firm* — Stetina Brunda Garred & Brucker

(57) ABSTRACT

Methods, systems and devices are described for providing mechanical ventilation support of a patient using an open airway patient interface. The system includes gas delivery circuit and patient interface configurations to optimize performance and efficiency of the ventilation system. A ventilation system may include a ventilator for supplying ventilation gas. A patient interface may include distal end in communication with a patient airway, a proximal end in communication with ambient air, and an airflow channel between the distal end and the proximal end. A gas delivery circuit may be adapted to attach to the patient interface without occluding the patient interface to allow ambient air to flow from outside the patient interface to the patient airway. The ventilation gas may entrain air from ambient and from the patient airway.

41 Claims, 16 Drawing Sheets

(56) References Cited

U.S. PATENT DOCUMENTS

| | | |
|---|---|---|
| 718,785 A | 1/1903 | McNary |
| 853,439 A | 5/1907 | Clark |
| 859,156 A | 7/1907 | Warnken |
| 909,002 A | 1/1909 | Lambert |
| 1,125,542 A | 1/1915 | Humphries |
| 1,129,619 A | 2/1915 | Zapf |
| 1,331,297 A | 2/1920 | Walker |
| 2,178,800 A | 11/1939 | Lombard |
| 2,259,817 A | 10/1941 | Hawkins |
| 2,552,595 A | 5/1951 | Seeler |
| 2,663,297 A | 12/1953 | Turnberg |
| 2,693,800 A | 11/1954 | Caldwell |
| 2,735,432 A | 2/1956 | Hudson |
| 2,792,000 A | 5/1957 | Richardson |
| 2,843,122 A | 7/1958 | Hudson |
| 2,859,748 A | 11/1958 | Hudson |
| 2,931,358 A | 4/1960 | Sheridan |
| 2,947,938 A | 8/1960 | Bennett |
| 3,172,407 A | 3/1965 | Von Pechmann |
| 3,267,935 A | 8/1966 | Andreasen et al. |
| 3,319,627 A | 5/1967 | Windsor |
| 3,357,424 A | 12/1967 | Schreiber |
| 3,357,427 A | 12/1967 | Wittke et al. |
| 3,357,428 A | 12/1967 | Carlson |
| 3,437,274 A | 4/1969 | Apri |
| 3,460,533 A | 8/1969 | Riú Plá |
| 3,493,703 A | 2/1970 | Finan |
| 3,513,844 A | 5/1970 | Smith |
| 3,610,247 A | 10/1971 | Jackson |
| 3,625,206 A | 12/1971 | Charnley |
| 3,625,207 A | 12/1971 | Agnew |
| 3,631,438 A | 12/1971 | Lewin |
| 3,643,660 A | 2/1972 | Hudson et al. |
| 3,657,740 A | 4/1972 | Cialone |
| 3,682,171 A | 8/1972 | Dali et al. |
| 3,721,233 A | 3/1973 | Montgomery et al. |
| 3,726,275 A | 4/1973 | Jackson et al. |
| 3,727,606 A | 4/1973 | Sielaff |
| 3,733,008 A | 5/1973 | Churchill et al. |
| 3,741,208 A | 6/1973 | Jonsson et al. |
| 3,754,552 A | 8/1973 | King |
| 3,794,026 A | 2/1974 | Jacobs |
| 3,794,072 A | 2/1974 | Diedrich et al. |
| 3,802,431 A | 4/1974 | Farr |
| 3,831,596 A | 8/1974 | Cavallo |
| 3,881,480 A | 5/1975 | Lafourcade |
| 3,896,800 A | 7/1975 | Cibulka |
| 3,903,881 A | 9/1975 | Weigl |
| 3,905,362 A | 9/1975 | Eyrick et al. |
| 3,949,749 A | 4/1976 | Stewart |
| 3,951,143 A | 4/1976 | Kitrilakis et al. |
| 3,961,627 A | 6/1976 | Ernst et al. |
| 3,972,327 A | 8/1976 | Ernst et al. |
| 3,985,131 A | 10/1976 | Buck et al. |
| 3,991,790 A | 11/1976 | Russell |
| 4,003,377 A | 1/1977 | Dahl |
| 4,036,253 A | 7/1977 | Fegan et al. |
| 4,054,133 A | 10/1977 | Myers |
| 4,067,328 A | 1/1978 | Manley |
| 4,106,505 A | 8/1978 | Salter et al. |
| 4,146,885 A | 3/1979 | Lawson, Jr. |
| 4,206,754 A | 6/1980 | Cox et al. |
| 4,211,086 A | 7/1980 | Leonard et al. |
| 4,216,769 A | 8/1980 | Grimes |
| 4,231,363 A | 11/1980 | Grimes |
| 4,231,365 A | 11/1980 | Scarberry |
| 4,256,101 A | 3/1981 | Ellestad |
| 4,261,355 A | 4/1981 | Glazener |
| 4,263,908 A | 4/1981 | Mizerak |
| 4,265,237 A | 5/1981 | Schwanbom et al. |
| 4,266,540 A | 5/1981 | Panzik et al. |
| 4,273,124 A | 6/1981 | Zimmerman |
| 4,274,162 A | 6/1981 | Joy et al. |
| 4,278,082 A | 7/1981 | Blackmer |
| 4,282,869 A | 8/1981 | Zidulka |
| 4,306,567 A | 12/1981 | Krasner |
| 4,323,064 A | 4/1982 | Hoenig et al. |
| 4,354,488 A | 10/1982 | Bartos |
| 4,365,636 A | 12/1982 | Barker |
| 4,367,735 A | 1/1983 | Dali |
| 4,377,162 A | 3/1983 | Staver |
| 4,393,869 A | 7/1983 | Boyarsky et al. |
| 4,406,283 A | 9/1983 | Bir |
| 4,411,267 A | 10/1983 | Heyman |
| 4,413,514 A | 11/1983 | Bowman |
| 4,421,113 A | 12/1983 | Gedeon et al. |
| 4,422,456 A | 12/1983 | Tiep |
| 4,449,523 A | 5/1984 | Szachowicz et al. |
| 4,454,880 A | 6/1984 | Muto et al. |
| 4,462,398 A | 7/1984 | Durkan et al. |
| 4,469,097 A | 9/1984 | Kelman |
| 4,481,944 A | 11/1984 | Bunnell |
| 4,488,548 A | 12/1984 | Agdanowski |
| 4,495,946 A | 1/1985 | Lemer |
| 4,506,666 A | 3/1985 | Durkan |
| 4,506,667 A | 3/1985 | Ansite |
| 4,519,387 A | 5/1985 | Durkan et al. |
| 4,520,812 A | 6/1985 | Freitag et al. |
| 4,527,557 A | 7/1985 | DeVries et al. |
| 4,535,766 A | 8/1985 | Baum |
| 4,537,188 A | 8/1985 | Phuc |
| 4,539,984 A | 9/1985 | Kiszel et al. |
| 4,548,590 A | 10/1985 | Green |
| 4,559,940 A | 12/1985 | McGinnis |
| 4,570,631 A | 2/1986 | Durkan |
| 4,571,741 A | 2/1986 | Guillaumot |
| 4,584,996 A | 4/1986 | Blum |
| 4,590,951 A | 5/1986 | O'Connor |
| 4,592,349 A | 6/1986 | Bird |
| 4,621,632 A | 11/1986 | Bartels et al. |
| 4,630,606 A | 12/1986 | Weerda et al. |
| 4,630,614 A | 12/1986 | Atlas |
| 4,644,947 A | 2/1987 | Whitwam et al. |
| 4,648,395 A | 3/1987 | Sato et al. |
| 4,648,398 A | 3/1987 | Agdanowski et al. |
| 4,658,832 A | 4/1987 | Brugnoli |
| 4,660,555 A | 4/1987 | Payton |
| 4,682,591 A | 7/1987 | Jones |
| 4,684,398 A | 8/1987 | Dunbar et al. |
| 4,686,974 A | 8/1987 | Sato et al. |
| 4,686,975 A | 8/1987 | Naimon et al. |
| 4,688,961 A | 8/1987 | Shioda et al. |
| 4,705,034 A | 11/1987 | Perkins |
| 4,744,356 A | 5/1988 | Greenwood |
| 4,747,403 A | 5/1988 | Gluck et al. |
| 4,753,233 A | 6/1988 | Grimes |
| 4,773,411 A | 9/1988 | Downs |
| 4,776,333 A | 10/1988 | Miyamae |
| 4,782,832 A | 11/1988 | Trimble et al. |
| 4,784,130 A | 11/1988 | Kenyon et al. |
| 4,803,981 A | 2/1989 | Vickery |
| 4,807,616 A | 2/1989 | Adahan |
| 4,807,617 A | 2/1989 | Nesti |
| 4,808,160 A | 2/1989 | Timmons et al. |
| 4,813,431 A | 3/1989 | Brown |
| 4,817,897 A | 4/1989 | Kreusel |
| 4,818,320 A | 4/1989 | Weichselbaum |
| 4,823,788 A | 4/1989 | Smith et al. |
| 4,825,859 A | 5/1989 | Lambert |
| 4,827,922 A | 5/1989 | Champain et al. |
| 4,832,014 A | 5/1989 | Perkins |
| 4,838,255 A | 6/1989 | Lambert |
| 4,841,953 A | 6/1989 | Dodrill |
| 4,848,333 A | 7/1989 | Waite |
| 4,850,350 A | 7/1989 | Jackson |
| 4,865,586 A | 9/1989 | Hedberg |
| 4,869,718 A | 9/1989 | Brader |
| 4,899,740 A | 2/1990 | Napolitano |
| 4,905,688 A | 3/1990 | Vicenzi et al. |
| 4,915,103 A | 4/1990 | Visveshwara et al. |
| 4,915,105 A | 4/1990 | Lee |
| 4,919,128 A | 4/1990 | Kopala et al. |
| 4,919,132 A | 4/1990 | Miser |
| 4,938,212 A | 7/1990 | Snook et al. |

(56) References Cited

U.S. PATENT DOCUMENTS

| | | |
|---|---|---|
| 4,944,310 A | 7/1990 | Sullivan |
| 4,967,743 A | 11/1990 | Lambert |
| 4,971,049 A | 11/1990 | Rotariu et al. |
| 4,982,735 A | 1/1991 | Yagata et al. |
| 4,986,269 A | 1/1991 | Hakkinen |
| 4,989,599 A | 2/1991 | Carter |
| 4,990,157 A | 2/1991 | Roberts et al. |
| 5,000,175 A | 3/1991 | Pue |
| 5,002,050 A | 3/1991 | McGinnis |
| 5,005,570 A | 4/1991 | Perkins |
| 5,018,519 A | 5/1991 | Brown |
| 5,022,394 A | 6/1991 | Chmielinski |
| 5,024,219 A | 6/1991 | Dietz |
| 5,025,805 A | 6/1991 | Nutter |
| 5,038,771 A | 8/1991 | Dietz |
| 5,042,478 A | 8/1991 | Kopala et al. |
| 5,046,491 A | 9/1991 | Derrick |
| 5,046,492 A | 9/1991 | Stackhouse et al. |
| 5,048,515 A | 9/1991 | Sanso |
| 5,048,516 A | 9/1991 | Soderberg |
| 5,052,400 A | 10/1991 | Dietz |
| 5,054,484 A | 10/1991 | Hebeler, Jr. |
| 5,058,580 A | 10/1991 | Hazard |
| 5,074,299 A | 12/1991 | Dietz |
| 5,076,267 A | 12/1991 | Pasternack |
| 5,090,408 A | 2/1992 | Spofford et al. |
| 5,097,827 A | 3/1992 | Izumi |
| 5,099,836 A | 3/1992 | Rowland et al. |
| 5,099,837 A | 3/1992 | Russel, Sr. et al. |
| 5,101,820 A | 4/1992 | Christopher |
| 5,103,815 A | 4/1992 | Siegel et al. |
| 5,105,807 A | 4/1992 | Kahn et al. |
| 5,107,830 A | 4/1992 | Younes |
| 5,107,831 A | 4/1992 | Halpern et al. |
| 5,113,857 A | 5/1992 | Dickerman et al. |
| 5,117,818 A | 6/1992 | Palfy |
| 5,117,819 A | 6/1992 | Servidio et al. |
| 5,127,400 A | 7/1992 | DeVries et al. |
| 5,134,995 A | 8/1992 | Gruenke et al. |
| 5,134,996 A | 8/1992 | Bell |
| 5,140,045 A | 8/1992 | Askanazi et al. |
| 5,148,802 A | 9/1992 | Sanders et al. |
| 5,161,525 A | 11/1992 | Kimm et al. |
| 5,165,397 A | 11/1992 | Arp |
| 5,181,509 A | 1/1993 | Spofford et al. |
| 5,184,610 A | 2/1993 | Marten et al. |
| 5,186,167 A | 2/1993 | Kolobow |
| 5,193,532 A | 3/1993 | Moa et al. |
| 5,193,533 A | 3/1993 | Body et al. |
| 5,199,424 A | 4/1993 | Sullivan et al. |
| 5,211,170 A | 5/1993 | Press |
| 5,217,008 A | 6/1993 | Lindholm |
| 5,233,978 A | 8/1993 | Callaway |
| 5,233,979 A | 8/1993 | Strickland |
| 5,239,994 A | 8/1993 | Atkins |
| 5,239,995 A | 8/1993 | Estes et al. |
| 5,243,972 A | 9/1993 | Huang |
| 5,245,995 A | 9/1993 | Sullivan et al. |
| 5,255,675 A | 10/1993 | Kolobow |
| 5,258,027 A | 11/1993 | Berghaus |
| 5,269,296 A | 12/1993 | Landis |
| 5,271,388 A | 12/1993 | Whitwam et al. |
| 5,271,391 A | 12/1993 | Graves |
| 5,275,159 A | 1/1994 | Griebel |
| 5,279,288 A | 1/1994 | Christopher |
| 5,287,852 A | 2/1994 | Arkinstall |
| 5,303,698 A | 4/1994 | Tobia et al. |
| 5,303,700 A | 4/1994 | Weismann et al. |
| 5,318,019 A | 6/1994 | Celaya |
| 5,331,995 A | 7/1994 | Westfall et al. |
| 5,335,656 A | 8/1994 | Bowe et al. |
| 5,339,809 A | 8/1994 | Beck, Jr. et al. |
| 5,349,946 A | 9/1994 | McComb |
| 5,368,017 A | 11/1994 | Sorenson et al. |
| 5,370,112 A | 12/1994 | Perkins |
| 5,373,842 A | 12/1994 | Olsson et al. |
| 5,375,593 A | 12/1994 | Press |
| 5,388,575 A | 2/1995 | Taube |
| 5,394,870 A | 3/1995 | Johansson |
| 5,398,676 A | 3/1995 | Press et al. |
| 5,398,682 A | 3/1995 | Lynn |
| 5,400,778 A | 3/1995 | Jonson et al. |
| 5,419,314 A | 5/1995 | Christopher |
| 5,438,979 A | 8/1995 | Johnson, Jr. et al. |
| 5,438,980 A | 8/1995 | Phillips |
| 5,443,075 A | 8/1995 | Holscher |
| 5,460,174 A | 10/1995 | Chang |
| 5,460,613 A | 10/1995 | Ulrich et al. |
| 5,474,062 A | 12/1995 | DeVires et al. |
| 5,477,852 A | 12/1995 | Landis et al. |
| 5,485,850 A | 1/1996 | Dietz |
| 5,490,502 A | 2/1996 | Rapoport et al. |
| 5,503,146 A | 4/1996 | Froehlich et al. |
| 5,503,497 A | 4/1996 | Dudley et al. |
| 5,507,282 A | 4/1996 | Younes |
| 5,509,409 A | 4/1996 | Weatherholt |
| 5,513,628 A | 5/1996 | Coles et al. |
| 5,513,631 A | 5/1996 | McWilliams |
| 5,513,635 A | 5/1996 | Bedi |
| 5,522,382 A | 6/1996 | Sullivan et al. |
| 5,526,806 A | 6/1996 | Sansoni |
| 5,529,060 A | 6/1996 | Salmon et al. |
| 5,533,506 A | 7/1996 | Wood |
| 5,535,738 A | 7/1996 | Estes et al. |
| 5,537,997 A | 7/1996 | Mechlenburg et al. |
| 5,538,002 A | 7/1996 | Boussignac et al. |
| 5,542,415 A | 8/1996 | Brody |
| 5,546,935 A | 8/1996 | Champeau |
| 5,549,106 A | 8/1996 | Gruenke et al. |
| 5,551,419 A | 9/1996 | Froehlich et al. |
| 5,558,086 A | 9/1996 | Smith et al. |
| 5,564,416 A | 10/1996 | Jones |
| 5,575,282 A | 11/1996 | Knoch et al. |
| 5,582,164 A | 12/1996 | Sanders |
| 5,593,143 A | 1/1997 | Ferrarin |
| 5,595,174 A | 1/1997 | Gwaltney |
| 5,598,837 A | 2/1997 | Sirianne, Jr. et al. |
| 5,598,840 A | 2/1997 | lund et al. |
| 5,603,315 A | 2/1997 | Sasso, Jr. |
| 5,605,148 A | 2/1997 | Jones |
| 5,626,131 A | 5/1997 | Chua et al. |
| 5,632,269 A | 5/1997 | Zdrojkowski |
| 5,636,630 A | 6/1997 | Miller et al. |
| 5,645,053 A | 7/1997 | Remmers et al. |
| 5,645,054 A | 7/1997 | Cotner et al. |
| 5,647,351 A | 7/1997 | Weismann et al. |
| 5,669,377 A | 9/1997 | Fenn |
| 5,669,380 A | 9/1997 | Garry et al. |
| 5,676,132 A | 10/1997 | Tillotson et al. |
| 5,676,135 A | 10/1997 | McClean |
| 5,682,878 A | 11/1997 | Ogden |
| 5,682,881 A | 11/1997 | Winthrop et al. |
| 5,687,713 A | 11/1997 | Bahr et al. |
| 5,687,714 A | 11/1997 | Kolobow et al. |
| 5,687,715 A | 11/1997 | Landis et al. |
| 5,690,097 A | 11/1997 | Howard et al. |
| 5,692,497 A | 12/1997 | Schnitzer et al. |
| 5,697,361 A * | 12/1997 | Smith .................... 128/204.25 |
| 5,697,364 A | 12/1997 | Chua et al. |
| 5,704,345 A | 1/1998 | Berthon-Jones |
| 5,711,296 A | 1/1998 | Kolobow |
| 5,715,812 A | 2/1998 | Deighan et al. |
| 5,715,815 A | 2/1998 | Lorenzen et al. |
| 5,720,278 A | 2/1998 | Lachmann et al. |
| 5,735,268 A | 4/1998 | Chua et al. |
| 5,735,272 A | 4/1998 | Dillon et al. |
| 5,740,796 A | 4/1998 | Skog |
| 5,752,511 A | 5/1998 | Simmons et al. |
| 5,762,638 A | 6/1998 | Shikani et al. |
| 5,791,337 A | 8/1998 | Coles et al. |
| 5,819,723 A | 10/1998 | Joseph |
| 5,826,579 A | 10/1998 | Remmers et al. |
| 5,845,636 A | 12/1998 | Gruenke et al. |
| 5,865,173 A | 2/1999 | Froehlich |

(56) References Cited

U.S. PATENT DOCUMENTS

| | | |
|---|---|---|
| 5,865,174 A | 2/1999 | Kloeppel |
| 5,881,723 A | 3/1999 | Wallace et al. |
| 5,904,648 A | 5/1999 | Arndt et al. |
| 5,906,204 A | 5/1999 | Beran et al. |
| 5,911,756 A | 6/1999 | Debry |
| 5,915,379 A | 6/1999 | Wallace et al. |
| 5,915,381 A | 6/1999 | Nord |
| 5,918,597 A | 7/1999 | Jones et al. |
| 5,921,238 A | 7/1999 | Bourdon |
| 5,921,942 A | 7/1999 | Remmers et al. |
| 5,921,952 A | 7/1999 | Desmond, III et al. |
| 5,927,276 A | 7/1999 | Rodriguez |
| 5,928,189 A | 7/1999 | Phillips et al. |
| 5,931,160 A | 8/1999 | Gilmore et al. |
| 5,931,162 A | 8/1999 | Christian |
| 5,937,853 A | 8/1999 | Strom |
| 5,937,855 A | 8/1999 | Zdrojkowski et al. |
| 5,938,118 A | 8/1999 | Cooper |
| 5,954,050 A | 9/1999 | Christopher |
| 5,957,136 A | 9/1999 | Magidson et al. |
| 5,964,223 A | 10/1999 | Baran |
| 5,975,077 A | 11/1999 | Hofstetter et al. |
| 5,975,081 A | 11/1999 | Hood et al. |
| 5,979,440 A | 11/1999 | Honkonen et al. |
| 5,989,193 A | 11/1999 | Sullivan |
| 6,000,396 A | 12/1999 | Melker et al. |
| 6,019,101 A | 2/2000 | Cotner et al. |
| 6,039,696 A | 3/2000 | Bell |
| 6,050,260 A | 4/2000 | Daniell et al. |
| 6,076,519 A | 6/2000 | Johnson |
| 6,085,747 A | 7/2000 | Axe et al. |
| 6,091,973 A | 7/2000 | Colla et al. |
| 6,093,169 A | 7/2000 | Cardoso |
| 6,105,575 A | 8/2000 | Estes et al. |
| 6,109,264 A | 8/2000 | Sauer |
| 6,112,746 A | 9/2000 | Kwok et al. |
| 6,119,694 A | 9/2000 | Correa et al. |
| 6,120,460 A | 9/2000 | Abreu |
| 6,123,668 A | 9/2000 | Abreu |
| 6,131,571 A | 10/2000 | Lampotang et al. |
| 6,135,970 A | 10/2000 | Kadhiresan et al. |
| 6,152,132 A | 11/2000 | Psaros |
| 6,152,134 A | 11/2000 | Webber et al. |
| 6,158,432 A | 12/2000 | Biondi et al. |
| 6,192,883 B1 | 2/2001 | Miller, Jr. |
| 6,203,502 B1 | 3/2001 | Hilgendorf et al. |
| 6,213,119 B1 | 4/2001 | Brydon et al. |
| 6,213,955 B1 | 4/2001 | Karakasoglu et al. |
| 6,220,244 B1 | 4/2001 | McLaughlin |
| 6,224,560 B1 | 5/2001 | Gazula et al. |
| 6,227,200 B1 | 5/2001 | Crump et al. |
| 6,247,470 B1 | 6/2001 | Ketchedjian |
| 6,269,811 B1 | 8/2001 | Duff et al. |
| 6,269,812 B1 | 8/2001 | Wallace et al. |
| 6,273,859 B1 | 8/2001 | Remmers et al. |
| 6,286,508 B1 | 9/2001 | Remmers et al. |
| D449,376 S | 10/2001 | McDonald et al. |
| D449,883 S | 10/2001 | McDonald et al. |
| 6,298,850 B1 | 10/2001 | Argraves |
| 6,305,374 B1 | 10/2001 | Zdrojkowski et al. |
| 6,314,957 B1 | 11/2001 | Boissin et al. |
| 6,315,739 B1 | 11/2001 | Merilainen et al. |
| D451,598 S | 12/2001 | McDonald et al. |
| 6,328,038 B1 | 12/2001 | Kessler et al. |
| 6,328,753 B1 | 12/2001 | Zammit |
| 6,332,463 B1 | 12/2001 | Farrugia et al. |
| 6,345,619 B1 | 2/2002 | Finn |
| 6,357,438 B1 | 3/2002 | Hansen |
| 6,357,440 B1 | 3/2002 | Hansen et al. |
| 6,360,741 B2 | 3/2002 | Truschel |
| 6,360,745 B1 | 3/2002 | Wallace et al. |
| 6,363,933 B1 | 4/2002 | Berthon-Jones |
| 6,367,474 B1 | 4/2002 | Berthon-Jones et al. |
| 6,369,838 B1 | 4/2002 | Wallace et al. |
| 6,371,114 B1 | 4/2002 | Schmidt et al. |
| 6,378,520 B1 | 4/2002 | Davenport |
| 6,390,091 B1 | 5/2002 | Banner et al. |
| 6,394,088 B1 | 5/2002 | Frye et al. |
| 6,398,739 B1 | 6/2002 | Sullivan et al. |
| 6,418,928 B1 | 7/2002 | Bordewick et al. |
| 6,422,240 B1 | 7/2002 | Levitsky et al. |
| 6,423,001 B1 | 7/2002 | Abreu |
| 6,427,690 B1 | 8/2002 | McCombs et al. |
| 6,431,172 B1 | 8/2002 | Bordewick |
| 6,439,228 B1 | 8/2002 | Hete et al. |
| 6,439,229 B1 | 8/2002 | Du et al. |
| 6,439,234 B1 | 8/2002 | Curti et al. |
| 6,439,235 B1 | 8/2002 | Larquet et al. |
| 6,450,164 B1 | 9/2002 | Banner et al. |
| 6,450,166 B1 | 9/2002 | McDonald et al. |
| 6,457,472 B1 | 10/2002 | Schwartz et al. |
| 6,467,477 B1 | 10/2002 | Frank et al. |
| 6,478,026 B1 | 11/2002 | Wood |
| 6,494,202 B2 | 12/2002 | Farmer |
| 6,494,206 B1 | 12/2002 | Bergamaschi et al. |
| 6,505,623 B1 | 1/2003 | Hansen |
| 6,505,624 B1 | 1/2003 | Campbell, Sr. |
| 6,516,801 B2 | 2/2003 | Boussignac |
| 6,520,176 B1 | 2/2003 | Dubois et al. |
| 6,520,183 B2 | 2/2003 | Amar |
| 6,530,373 B1 | 3/2003 | Patron et al. |
| 6,532,958 B1 | 3/2003 | Buan et al. |
| 6,532,960 B1 | 3/2003 | Yurko |
| 6,536,432 B2 | 3/2003 | Truschel |
| 6,536,436 B1 | 3/2003 | McGlothen |
| 6,550,478 B2 | 4/2003 | Remmers et al. |
| 6,553,992 B1 | 4/2003 | Berthon-Jones et al. |
| 6,561,188 B1 | 5/2003 | Ellis |
| 6,561,193 B1 | 5/2003 | Noble |
| 6,564,797 B1 | 5/2003 | Mechlenburg et al. |
| 6,564,800 B1 | 5/2003 | Olivares |
| 6,568,391 B1 | 5/2003 | Tatarek et al. |
| 6,571,794 B1 | 6/2003 | Hansen |
| 6,571,796 B2 | 6/2003 | Banner et al. |
| 6,571,798 B1 | 6/2003 | Thornton |
| 6,575,159 B1 | 6/2003 | Frye et al. |
| 6,575,944 B1 | 6/2003 | McNary et al. |
| 6,584,973 B1 | 7/2003 | Biondi et al. |
| 6,588,422 B1 | 7/2003 | Berthon-Jones et al. |
| 6,588,423 B1 | 7/2003 | Sinderby |
| 6,591,834 B1 | 7/2003 | Colla et al. |
| 6,591,835 B1 | 7/2003 | Blanch |
| 6,595,207 B1 | 7/2003 | McDonald et al. |
| 6,595,215 B2 | 7/2003 | Wood |
| 6,609,517 B1 | 8/2003 | Estes et al. |
| 6,622,726 B1 | 9/2003 | Du |
| 6,626,174 B1 | 9/2003 | Genger et al. |
| 6,626,175 B2 | 9/2003 | Jafari et al. |
| 6,629,525 B2 | 10/2003 | Hill et al. |
| 6,629,527 B1 | 10/2003 | Estes et al. |
| 6,629,529 B2 | 10/2003 | Arnott |
| 6,631,919 B1 | 10/2003 | West et al. |
| 6,634,356 B1 | 10/2003 | O'Dea et al. |
| 6,635,021 B1 | 10/2003 | Sullivan et al. |
| 6,640,806 B2 | 11/2003 | Yurko |
| 6,644,305 B2 | 11/2003 | MacRae et al. |
| 6,644,311 B1 | 11/2003 | Truitt et al. |
| 6,644,315 B2 | 11/2003 | Ziaee |
| 6,651,653 B1 | 11/2003 | Honkonen et al. |
| 6,651,656 B2 | 11/2003 | Demers et al. |
| 6,651,658 B1 | 11/2003 | Hill et al. |
| 6,655,382 B1 | 12/2003 | Kolobow |
| 6,655,385 B1 | 12/2003 | Curti et al. |
| 6,666,208 B1 | 12/2003 | Schumacher et al. |
| 6,668,828 B1 | 12/2003 | Figley et al. |
| 6,668,829 B2 | 12/2003 | Biondi et al. |
| 6,669,712 B1 | 12/2003 | Cardoso |
| 6,675,796 B2 | 1/2004 | McDonald |
| 6,675,801 B2 | 1/2004 | Wallace et al. |
| 6,679,265 B2 | 1/2004 | Strickland et al. |
| 6,681,764 B1 | 1/2004 | Honkonen et al. |
| 6,684,883 B1 | 2/2004 | Burns |
| 6,691,702 B2 | 2/2004 | Appel et al. |
| 6,691,707 B1 | 2/2004 | Gunaratnam et al. |

(56) References Cited

U.S. PATENT DOCUMENTS

| | | | |
|---|---|---|---|
| 6,694,973 B1 | 2/2004 | Dunhao et al. |
| 6,694,978 B1 | 2/2004 | Bennarsten |
| 6,698,423 B1 | 3/2004 | Honkonen et al. |
| 6,705,314 B1 | 3/2004 | O'Dea |
| 6,705,315 B2 | 3/2004 | Sullivan et al. |
| 6,722,360 B2 | 4/2004 | Doshi |
| 6,722,362 B2 | 4/2004 | Hete et al. |
| 6,742,517 B1 | 6/2004 | Frye et al. |
| 6,745,768 B2 | 6/2004 | Colla et al. |
| 6,752,150 B1 | 6/2004 | Remmers et al. |
| 6,752,151 B2 | 6/2004 | Hill |
| 6,752,152 B2 | 6/2004 | Gale et al. |
| 6,755,193 B2 | 6/2004 | Berthon-Jones et al. |
| 6,758,217 B1 | 7/2004 | Younes |
| 6,761,172 B2 | 7/2004 | Boussignac et al. |
| 6,763,832 B1 | 7/2004 | Kirsch et al. |
| 6,769,432 B1 | 8/2004 | Keifer |
| 6,776,162 B2 | 8/2004 | Wood |
| 6,776,163 B2 | 8/2004 | Dougill et al. |
| 6,789,539 B2 | 9/2004 | Martinez |
| 6,796,305 B1 | 9/2004 | Banner et al. |
| 6,799,575 B1 | 10/2004 | Carter |
| 6,805,126 B2 | 10/2004 | Dutkiewicz |
| 6,807,966 B2 | 10/2004 | Wright |
| 6,807,967 B2 | 10/2004 | Wood |
| 6,810,876 B2 | 11/2004 | Berthon-Jones |
| 6,814,073 B2 | 11/2004 | Wickham |
| 6,814,077 B1 | 11/2004 | Eistert |
| 6,823,866 B2 | 11/2004 | Jafari et al. |
| 6,827,340 B2 | 12/2004 | Austin et al. |
| 6,837,238 B2 | 1/2005 | McDonald |
| 6,840,240 B1 | 1/2005 | Berthon-Jones et al. |
| 6,843,247 B2 | 1/2005 | Frye et al. |
| 6,848,446 B2 | 2/2005 | Noble |
| 6,854,462 B2 | 2/2005 | Berthon-Jones et al. |
| 6,863,069 B2 | 3/2005 | Wood |
| 6,866,041 B2 | 3/2005 | Hardy, Jr. et al. |
| 6,877,511 B2 | 4/2005 | DeVries et al. |
| 6,880,556 B2 | 4/2005 | Uchiyama et al. |
| 6,910,480 B1 | 6/2005 | Berthon-Jones |
| 6,910,482 B2 | 6/2005 | Bliss et al. |
| 6,910,510 B2 | 6/2005 | Gale et al. |
| 6,913,601 B2 | 7/2005 | St. Goar et al. |
| 6,915,803 B2 | 7/2005 | Berthon-Jones et al. |
| 6,920,875 B1 | 7/2005 | Hill et al. |
| 6,920,877 B2 | 7/2005 | Remmers et al. |
| 6,920,878 B2 | 7/2005 | Sinderby et al. |
| 6,932,084 B2 | 8/2005 | Estes et al. |
| 6,938,619 B1 | 9/2005 | Hickle |
| 6,938,620 B2 | 9/2005 | Payne, Jr. |
| 6,941,950 B2 | 9/2005 | Wilson et al. |
| 6,948,497 B2 | 9/2005 | Zdrojkowski et al. |
| 6,951,217 B2 | 10/2005 | Berthon-Jones |
| 6,971,382 B1 | 12/2005 | Corso |
| 6,986,353 B2 | 1/2006 | Wright |
| 6,994,089 B2 | 2/2006 | Wood |
| 6,997,177 B2 | 2/2006 | Wood |
| 6,997,881 B2 | 2/2006 | Green et al. |
| 7,000,612 B2 | 2/2006 | Jafari et al. |
| 7,004,170 B1 | 2/2006 | Gillstrom |
| 7,007,692 B2 | 3/2006 | Aylsworth et al. |
| 7,011,091 B2 | 3/2006 | Hill et al. |
| 7,013,892 B2 | 3/2006 | Estes et al. |
| 7,013,898 B2 | 3/2006 | Rashad et al. |
| 7,017,574 B2 | 3/2006 | Biondi et al. |
| 7,017,575 B2 | 3/2006 | Yagi et al. |
| 7,024,945 B2 | 4/2006 | Wallace |
| 7,036,504 B2 | 5/2006 | Wallace et al. |
| 7,044,129 B1 | 5/2006 | Truschel et al. |
| 7,047,969 B2 | 5/2006 | Noble |
| 7,047,974 B2 | 5/2006 | Strickland et al. |
| 7,051,735 B2 | 5/2006 | Mechlenburg et al. |
| 7,055,522 B2 | 6/2006 | Berthon-Jones |
| 7,059,328 B2 | 6/2006 | Wood |
| 7,066,173 B2 | 6/2006 | Banner et al. |
| 7,066,178 B2 | 6/2006 | Gunaratnam et al. |
| 7,077,132 B2 | 7/2006 | Berthon-Jones |
| 7,077,133 B2 | 7/2006 | Yagi et al. |
| 7,080,645 B2 | 7/2006 | Genger et al. |
| 7,080,646 B2 | 7/2006 | Wiesmann et al. |
| 7,100,607 B2 | 9/2006 | Zdrojkowski et al. |
| 7,100,609 B2 | 9/2006 | Berthon-Jones et al. |
| 7,117,438 B2 | 10/2006 | Wallace et al. |
| 7,121,277 B2 | 10/2006 | Strom |
| 7,128,578 B2 | 10/2006 | Lampotang et al. |
| 7,152,598 B2 | 12/2006 | Morris et al. |
| 7,152,604 B2 | 12/2006 | Hickle et al. |
| 7,156,090 B2 | 1/2007 | Nomori |
| 7,156,097 B2 | 1/2007 | Cardoso |
| 7,162,296 B2 | 1/2007 | Leonhardt et al. |
| 7,168,429 B2 | 1/2007 | Matthews et al. |
| 7,188,621 B2 | 3/2007 | DeVries et al. |
| 7,188,624 B2 | 3/2007 | Wood |
| 7,195,016 B2 | 3/2007 | Loyd et al. |
| 7,195,018 B1 | 3/2007 | Goldstein |
| 7,201,169 B2 | 4/2007 | Wilkie et al. |
| 7,201,269 B2 | 4/2007 | Buscher et al. |
| D542,912 S | 5/2007 | Gunaratnam et al. |
| 7,222,623 B2 | 5/2007 | DeVries et al. |
| 7,225,811 B2 | 6/2007 | Ruiz et al. |
| 7,234,465 B2 | 6/2007 | Wood |
| 7,237,205 B2 | 6/2007 | Sarel |
| 7,246,620 B2 | 7/2007 | Conroy, Jr. |
| D549,323 S | 8/2007 | Kwok et al. |
| 7,255,103 B2 | 8/2007 | Bassin |
| 7,255,107 B1 | 8/2007 | Gomez |
| 7,267,122 B2 | 9/2007 | Hill |
| 7,267,123 B2 | 9/2007 | Aylsworth et al. |
| 7,270,126 B2 | 9/2007 | Wallace et al. |
| 7,270,128 B2 | 9/2007 | Berthon-Jones et al. |
| 7,296,569 B2 | 11/2007 | Frye et al. |
| 7,296,573 B2 | 11/2007 | Estes et al. |
| D557,802 S | 12/2007 | Miceli, Jr. et al. |
| 7,302,950 B2 | 12/2007 | Berthon-Jones et al. |
| 7,305,987 B2 | 12/2007 | Scholler et al. |
| 7,318,437 B2 | 1/2008 | Gunaratnam et al. |
| 7,320,321 B2 | 1/2008 | Pranger et al. |
| 7,328,703 B1 | 2/2008 | Tiep |
| 7,353,826 B2 | 4/2008 | Sleeper et al. |
| 7,367,337 B2 | 5/2008 | Berthon-Jones et al. |
| 7,370,652 B2 | 5/2008 | Matula, Jr. et al. |
| 7,373,939 B1 | 5/2008 | DuBois et al. |
| 7,406,966 B2 | 8/2008 | Wondka |
| 7,418,965 B2 | 9/2008 | Fukunaga et al. |
| 7,422,015 B2 | 9/2008 | Delisle et al. |
| 7,431,035 B2 | 10/2008 | Mizuta et al. |
| 7,451,762 B2 | 11/2008 | Chua et al. |
| 7,455,717 B2 | 11/2008 | Sprinkle |
| 7,461,656 B2 | 12/2008 | Gunaratnam et al. |
| 7,468,040 B2 | 12/2008 | Hartley et al. |
| 7,469,697 B2 | 12/2008 | Lee et al. |
| 7,472,702 B2 | 1/2009 | Beck et al. |
| 7,478,641 B2 | 1/2009 | Rousselet |
| 7,481,219 B2 | 1/2009 | Lewis et al. |
| 7,481,221 B2 | 1/2009 | Kullik et al. |
| 7,487,774 B2 | 2/2009 | Acker |
| 7,487,778 B2 | 2/2009 | Freitag |
| 7,490,605 B2 | 2/2009 | Frye et al. |
| D588,258 S | 3/2009 | Judson et al. |
| D589,139 S | 3/2009 | Guney et al. |
| 7,500,482 B2 | 3/2009 | Biederman |
| 7,509,957 B2 | 3/2009 | Duquette et al. |
| D591,419 S | 4/2009 | Chandran et al. |
| 7,533,670 B1 | 5/2009 | Freitag et al. |
| 7,556,038 B2 | 7/2009 | Kirby et al. |
| 7,559,327 B2 | 7/2009 | Hernandez |
| 7,562,657 B2 | 7/2009 | Blanch et al. |
| 7,562,659 B2 | 7/2009 | Matarasso |
| 7,578,294 B2 | 8/2009 | Pierro et al. |
| 7,588,033 B2 | 9/2009 | Wondka |
| 7,591,265 B2 | 9/2009 | Lee et al. |
| 7,631,642 B2 | 12/2009 | Freitag et al. |
| 7,640,934 B2 | 1/2010 | Zollinger et al. |
| 7,658,189 B2 | 2/2010 | Davidson et al. |

(56) References Cited

U.S. PATENT DOCUMENTS

| | | |
|---|---|---|
| D614,288 S | 4/2010 | Judson et al. |
| 7,721,733 B2 | 5/2010 | Hughes et al. |
| 7,721,736 B2 | 5/2010 | Urias et al. |
| 7,740,013 B2 | 6/2010 | Ishizaki et al. |
| 7,743,770 B2 | 6/2010 | Curti et al. |
| 7,762,253 B2 | 7/2010 | Acker et al. |
| 7,766,009 B2 | 8/2010 | Frye et al. |
| 7,787,946 B2 | 8/2010 | Stahmann et al. |
| 7,814,906 B2 | 10/2010 | Moretti |
| 7,819,120 B2 | 10/2010 | Taylor et al. |
| D626,646 S | 11/2010 | Lubke et al. |
| D627,059 S | 11/2010 | Wood et al. |
| 7,832,400 B2 | 11/2010 | Curti et al. |
| 7,837,761 B2 | 11/2010 | Bliss et al. |
| 7,841,343 B2 | 11/2010 | Deane et al. |
| 7,845,350 B1 | 12/2010 | Kayyali et al. |
| 7,849,854 B2 | 12/2010 | DeVries et al. |
| 7,856,982 B2 | 12/2010 | Matula, Jr. et al. |
| 7,866,318 B2 | 1/2011 | Bassin |
| 7,874,290 B2 | 1/2011 | Chalvignac |
| 7,874,291 B2 | 1/2011 | Ging et al. |
| 7,874,293 B2 | 1/2011 | Gunaratnam et al. |
| 7,878,980 B2 | 2/2011 | Ricciardelli |
| 7,882,834 B2 | 2/2011 | Gradon et al. |
| 7,886,740 B2 | 2/2011 | Thomas et al. |
| 7,891,353 B2 | 2/2011 | Chalvignac |
| 7,891,357 B2 | 2/2011 | Carron et al. |
| 7,896,958 B2 | 3/2011 | Sermet et al. |
| 7,900,627 B2 | 3/2011 | Aylsworth et al. |
| 7,900,628 B2 | 3/2011 | Matula, Jr. et al. |
| 7,900,635 B2 | 3/2011 | Gunaratnam et al. |
| 7,901,361 B2 | 3/2011 | Rapoport et al. |
| 7,905,231 B2 | 3/2011 | Chalvignac |
| 7,913,691 B2 | 3/2011 | Farrugia |
| 7,914,459 B2 | 3/2011 | Green et al. |
| 7,918,226 B2 | 4/2011 | Acker et al. |
| 7,926,486 B2 | 4/2011 | Childers |
| 7,926,487 B2 | 4/2011 | Drew et al. |
| 7,931,023 B2 | 4/2011 | Berthon-Jones et al. |
| 7,934,499 B2 | 5/2011 | Berthon-Jones |
| 7,938,114 B2 | 5/2011 | Matthews et al. |
| 7,942,150 B2 | 5/2011 | Guney et al. |
| 7,942,380 B2 | 5/2011 | Bertinetti et al. |
| 7,958,892 B2 | 6/2011 | Kwok et al. |
| 7,975,694 B2 | 7/2011 | Ho |
| 7,980,245 B2 | 7/2011 | Rice et al. |
| 7,987,847 B2 | 8/2011 | Wickham et al. |
| 7,987,850 B2 | 8/2011 | Zollinger et al. |
| 7,987,851 B2 | 8/2011 | Blom et al. |
| 7,992,557 B2 | 8/2011 | Nadjafizadeh et al. |
| 7,997,270 B2 | 8/2011 | Meier |
| 7,997,271 B2 | 8/2011 | Hickle et al. |
| 7,997,272 B2 | 8/2011 | Isaza |
| 8,001,967 B2 | 8/2011 | Wallace et al. |
| D645,557 S | 9/2011 | Scheiner et al. |
| 8,011,365 B2 | 9/2011 | Douglas et al. |
| 8,011,366 B2 | 9/2011 | Knepper |
| 8,015,971 B2 | 9/2011 | Kwok |
| 8,015,974 B2 | 9/2011 | Christopher et al. |
| 8,020,558 B2 | 9/2011 | Christopher et al. |
| 8,025,052 B2 | 9/2011 | Matthews et al. |
| RE42,843 E | 10/2011 | Strickland et al. |
| 8,042,535 B2 | 10/2011 | Kenyon et al. |
| 8,042,537 B2 | 10/2011 | Mechlenburg et al. |
| 8,042,539 B2 | 10/2011 | Chandran et al. |
| 8,042,546 B2 | 10/2011 | Gunaratnam et al. |
| 8,061,354 B2 | 11/2011 | Schneider et al. |
| 8,066,004 B2 | 11/2011 | Morris et al. |
| 2001/0035185 A1 | 11/2001 | Christopher |
| 2001/0035186 A1 | 11/2001 | Hill |
| 2001/0042548 A1 | 11/2001 | Boussignac |
| 2002/0014241 A1 | 2/2002 | Gradon et al. |
| 2002/0017300 A1 | 2/2002 | Hickle et al. |
| 2002/0020930 A1 | 2/2002 | Austin et al. |
| 2002/0026941 A1 | 3/2002 | Biondi et al. |
| 2002/0043264 A1 | 4/2002 | Wickham |
| 2002/0046751 A1 | 4/2002 | MacRae et al. |
| 2002/0046755 A1 | 4/2002 | De Voss |
| 2002/0046756 A1 | 4/2002 | Laizzo et al. |
| 2002/0053346 A1 | 5/2002 | Curti et al. |
| 2002/0055685 A1 | 5/2002 | Levitsky et al. |
| 2002/0059935 A1 | 5/2002 | Wood |
| 2002/0066452 A1 | 6/2002 | Kessler et al. |
| 2002/0078957 A1 | 6/2002 | Remmers et al. |
| 2002/0092527 A1 | 7/2002 | Wood |
| 2002/0112730 A1 | 8/2002 | Dutkiewicz |
| 2002/0153010 A1 | 10/2002 | Rozenberg et al. |
| 2002/0157673 A1 | 10/2002 | Kessler et al. |
| 2002/0159323 A1 | 10/2002 | Makabe et al. |
| 2002/0179090 A1 | 12/2002 | Boussignac |
| 2003/0000522 A1 | 1/2003 | Lynn et al. |
| 2003/0047185 A1 | 3/2003 | Olsen et al. |
| 2003/0069489 A1 | 4/2003 | Abreu |
| 2003/0079749 A1 | 5/2003 | Strickland et al. |
| 2003/0094178 A1 | 5/2003 | McAuley et al. |
| 2003/0111081 A1 | 6/2003 | Gupta |
| 2003/0116163 A1 | 6/2003 | Wood |
| 2003/0121519 A1 | 7/2003 | Estes et al. |
| 2003/0145852 A1 | 8/2003 | Schmidt et al. |
| 2003/0145853 A1 | 8/2003 | Muellner |
| 2003/0145856 A1 | 8/2003 | Zdrojkowski et al. |
| 2003/0150455 A1 | 8/2003 | Bliss et al. |
| 2003/0159696 A1 | 8/2003 | Boussignac et al. |
| 2003/0159697 A1 | 8/2003 | Wallace |
| 2003/0168067 A1 | 9/2003 | Dougill et al. |
| 2003/0213488 A1 | 11/2003 | Remmers et al. |
| 2003/0221687 A1 | 12/2003 | Kaigler |
| 2003/0230308 A1 | 12/2003 | Linden |
| 2004/0020493 A1 | 2/2004 | Wood |
| 2004/0025881 A1 | 2/2004 | Gunaratnam et al. |
| 2004/0035431 A1 | 2/2004 | Wright |
| 2004/0040560 A1 | 3/2004 | Euliano et al. |
| 2004/0050387 A1 | 3/2004 | Younes |
| 2004/0074494 A1 | 4/2004 | Frater |
| 2004/0159323 A1 | 8/2004 | Schmidt et al. |
| 2004/0206352 A1 | 10/2004 | Conroy |
| 2004/0221848 A1 | 11/2004 | Hill |
| 2004/0221854 A1 | 11/2004 | Hete et al. |
| 2004/0226566 A1 | 11/2004 | Gunaratnam et al. |
| 2004/0231674 A1 | 11/2004 | Tanaka |
| 2004/0237963 A1 | 12/2004 | Berthon-Jones |
| 2004/0254501 A1 | 12/2004 | Mault |
| 2004/0255943 A1 | 12/2004 | Morris et al. |
| 2005/0005938 A1 | 1/2005 | Berthon-Jones et al. |
| 2005/0010125 A1 | 1/2005 | Joy et al. |
| 2005/0011524 A1 | 1/2005 | Thomlinson et al. |
| 2005/0016534 A1 | 1/2005 | Ost |
| 2005/0033247 A1 | 2/2005 | Thompson |
| 2005/0034724 A1 | 2/2005 | O'Dea |
| 2005/0061318 A1* | 3/2005 | Faram ............... 128/204.18 |
| 2005/0061322 A1 | 3/2005 | Freitag |
| 2005/0061326 A1 | 3/2005 | Payne |
| 2005/0072430 A1 | 4/2005 | Djupesland |
| 2005/0081849 A1 | 4/2005 | Warren |
| 2005/0087190 A1 | 4/2005 | Jafari et al. |
| 2005/0098179 A1 | 5/2005 | Burton et al. |
| 2005/0103343 A1 | 5/2005 | Gosweiler |
| 2005/0121033 A1 | 6/2005 | Starr et al. |
| 2005/0121037 A1 | 6/2005 | Wood |
| 2005/0121038 A1 | 6/2005 | Christopher |
| 2005/0150498 A1 | 7/2005 | McDonald |
| 2005/0161049 A1 | 7/2005 | Wright |
| 2005/0166924 A1 | 8/2005 | Thomas et al. |
| 2005/0199242 A1 | 9/2005 | Matula et al. |
| 2005/0205096 A1 | 9/2005 | Matula et al. |
| 2005/0247308 A1 | 11/2005 | Frye et al. |
| 2005/0257793 A1 | 11/2005 | Tatsumoto |
| 2005/0274381 A1 | 12/2005 | Deane et al. |
| 2006/0005834 A1 | 1/2006 | Aylsworth et al. |
| 2006/0005842 A1 | 1/2006 | Rashad et al. |
| 2006/0011199 A1 | 1/2006 | Rashad et al. |
| 2006/0027234 A1 | 2/2006 | Gradon et al. |
| 2006/0048781 A1 | 3/2006 | Nawata |
| 2006/0054169 A1 | 3/2006 | Han et al. |

(56) References Cited

U.S. PATENT DOCUMENTS

| | | |
|---|---|---|
| 2006/0070625 A1 | 4/2006 | Ayappa et al. |
| 2006/0079799 A1 | 4/2006 | Green et al. |
| 2006/0096596 A1 | 5/2006 | Occhialini et al. |
| 2006/0107958 A1 | 5/2006 | Sleeper |
| 2006/0112959 A1 | 6/2006 | Mechlenburg et al. |
| 2006/0124131 A1 | 6/2006 | Chandran et al. |
| 2006/0124134 A1 | 6/2006 | Wood |
| 2006/0137690 A1 | 6/2006 | Gunaratnam et al. |
| 2006/0144396 A1 | 7/2006 | DeVries et al. |
| 2006/0149144 A1 | 7/2006 | Lynn et al. |
| 2006/0150972 A1 | 7/2006 | Mizuta et al. |
| 2006/0150973 A1 | 7/2006 | Chalvignac |
| 2006/0150982 A1 | 7/2006 | Wood |
| 2006/0174877 A1 | 8/2006 | Jagger et al. |
| 2006/0180149 A1 | 8/2006 | Matarasso |
| 2006/0185669 A1 | 8/2006 | Bassovitch |
| 2006/0196510 A1* | 9/2006 | McDonald et al. ......... 128/206.21 |
| 2006/0201504 A1 | 9/2006 | Singhal et al. |
| 2006/0213518 A1 | 9/2006 | DeVries et al. |
| 2006/0213519 A1 | 9/2006 | Schmidt et al. |
| 2006/0225737 A1 | 10/2006 | Iobbi |
| 2006/0237013 A1 | 10/2006 | Kwok |
| 2006/0243278 A1 | 11/2006 | Hamilton et al. |
| 2006/0249155 A1 | 11/2006 | Gambone |
| 2006/0266361 A1 | 11/2006 | Hernandez |
| 2006/0283447 A1* | 12/2006 | Dhuper et al. ............ 128/203.12 |
| 2007/0000490 A1 | 1/2007 | DeVries et al. |
| 2007/0000495 A1 | 1/2007 | Matula et al. |
| 2007/0017515 A1 | 1/2007 | Wallace et al. |
| 2007/0056590 A1 | 3/2007 | Wolfson |
| 2007/0062529 A1 | 3/2007 | Choncholas et al. |
| 2007/0068528 A1 | 3/2007 | Bohm et al. |
| 2007/0074724 A1 | 4/2007 | Duquette et al. |
| 2007/0084465 A1* | 4/2007 | Heinrich et al. ......... 128/204.25 |
| 2007/0089743 A1 | 4/2007 | Hoffman |
| 2007/0089745 A1 | 4/2007 | Gabriel et al. |
| 2007/0095347 A1 | 5/2007 | Lampotang et al. |
| 2007/0107728 A1 | 5/2007 | Ricciardelli et al. |
| 2007/0107732 A1 | 5/2007 | Dennis et al. |
| 2007/0107737 A1 | 5/2007 | Landis et al. |
| 2007/0113850 A1 | 5/2007 | Acker et al. |
| 2007/0113856 A1 | 5/2007 | Acker et al. |
| 2007/0125379 A1 | 6/2007 | Pierro et al. |
| 2007/0137653 A1 | 6/2007 | Wood |
| 2007/0163600 A1 | 7/2007 | Hoffman |
| 2007/0173705 A1 | 7/2007 | Teller et al. |
| 2007/0181125 A1 | 8/2007 | Mulier |
| 2007/0193705 A1 | 8/2007 | Hsu |
| 2007/0199568 A1 | 8/2007 | Diekens et al. |
| 2007/0209662 A1 | 9/2007 | Bowen et al. |
| 2007/0215156 A1 | 9/2007 | Kwok |
| 2007/0232950 A1 | 10/2007 | West |
| 2007/0240716 A1 | 10/2007 | Marx |
| 2007/0251528 A1 | 11/2007 | Seitz et al. |
| 2007/0272249 A1 | 11/2007 | Chandran et al. |
| 2008/0000475 A1 | 1/2008 | Hill |
| 2008/0006271 A1 | 1/2008 | Aylsworth et al. |
| 2008/0011298 A1 | 1/2008 | Mazar et al. |
| 2008/0011301 A1 | 1/2008 | Qian |
| 2008/0041371 A1 | 2/2008 | Freitag |
| 2008/0041386 A1 | 2/2008 | Dodier et al. |
| 2008/0045815 A1 | 2/2008 | Derchak et al. |
| 2008/0047559 A1 | 2/2008 | Fiori |
| 2008/0051674 A1 | 2/2008 | Davenport et al. |
| 2008/0053438 A1 | 3/2008 | DeVries et al. |
| 2008/0053447 A1 | 3/2008 | Ratajczak et al. |
| 2008/0060646 A1 | 3/2008 | Isaza |
| 2008/0060657 A1 | 3/2008 | McAuley et al. |
| 2008/0066753 A1 | 3/2008 | Martin et al. |
| 2008/0072902 A1 | 3/2008 | Setzer et al. |
| 2008/0078392 A1 | 4/2008 | Pelletier et al. |
| 2008/0078407 A1 | 4/2008 | Sherman |
| 2008/0092904 A1 | 4/2008 | Gunarathnam et al. |
| 2008/0092905 A1 | 4/2008 | Gunarathnam et al. |
| 2008/0092906 A1 | 4/2008 | Gunarathnam et al. |
| 2008/0099024 A1 | 5/2008 | Gunarathnam et al. |
| 2008/0099027 A1 | 5/2008 | Gunarathnam et al. |
| 2008/0105264 A1 | 5/2008 | Gunarathnam et al. |
| 2008/0110462 A1 | 5/2008 | Chekal et al. |
| 2008/0121230 A1 | 5/2008 | Cortez et al. |
| 2008/0135044 A1 | 6/2008 | Freitag et al. |
| 2008/0142019 A1 | 6/2008 | Lewis et al. |
| 2008/0161653 A1 | 7/2008 | Lin et al. |
| 2008/0173304 A1 | 7/2008 | Zaiser et al. |
| 2008/0178880 A1 | 7/2008 | Christopher et al. |
| 2008/0178881 A1 | 7/2008 | Whitcher et al. |
| 2008/0178882 A1 | 7/2008 | Christopher et al. |
| 2008/0185002 A1 | 8/2008 | Berthon-Jones et al. |
| 2008/0185007 A1 | 8/2008 | Sleeper et al. |
| 2008/0190429 A1 | 8/2008 | Tatarek |
| 2008/0190436 A1 | 8/2008 | Jaffe et al. |
| 2008/0196715 A1 | 8/2008 | Yamamori |
| 2008/0196723 A1 | 8/2008 | Tilley |
| 2008/0196728 A1 | 8/2008 | Ho |
| 2008/0202528 A1 | 8/2008 | Carter et al. |
| 2008/0216834 A1 | 9/2008 | Easley et al. |
| 2008/0216838 A1 | 9/2008 | Wondka |
| 2008/0216841 A1 | 9/2008 | Grimes et al. |
| 2008/0223369 A1 | 9/2008 | Warren |
| 2008/0245369 A1 | 10/2008 | Matula et al. |
| 2008/0251079 A1 | 10/2008 | Richey |
| 2008/0264417 A1 | 10/2008 | Manigel et al. |
| 2008/0283060 A1 | 11/2008 | Bassin |
| 2008/0295846 A1 | 12/2008 | Han et al. |
| 2008/0302364 A1 | 12/2008 | Garde et al. |
| 2008/0308104 A1 | 12/2008 | Blomberg et al. |
| 2009/0007911 A1 | 1/2009 | Cleary et al. |
| 2009/0020121 A1 | 1/2009 | Bassin |
| 2009/0044808 A1 | 2/2009 | Guney et al. |
| 2009/0056708 A1 | 3/2009 | Stenzler et al. |
| 2009/0078255 A1 | 3/2009 | Bowman et al. |
| 2009/0078258 A1 | 3/2009 | Bowman et al. |
| 2009/0095298 A1 | 4/2009 | Gunaratnam et al. |
| 2009/0095300 A1 | 4/2009 | McMorrow |
| 2009/0095303 A1 | 4/2009 | Sher et al. |
| 2009/0099471 A1 | 4/2009 | Broadley et al. |
| 2009/0101147 A1 | 4/2009 | Landis et al. |
| 2009/0101154 A1 | 4/2009 | Mutti et al. |
| 2009/0107502 A1 | 4/2009 | Younes |
| 2009/0118632 A1 | 5/2009 | Goepp |
| 2009/0120437 A1 | 5/2009 | Oates et al. |
| 2009/0126739 A1 | 5/2009 | Ng et al. |
| 2009/0133699 A1 | 5/2009 | Nalagatla et al. |
| 2009/0139527 A1 | 6/2009 | Ng et al. |
| 2009/0145435 A1 | 6/2009 | White et al. |
| 2009/0151719 A1 | 6/2009 | Wondka et al. |
| 2009/0151724 A1 | 6/2009 | Wondka et al. |
| 2009/0151726 A1 | 6/2009 | Freitag |
| 2009/0151729 A1 | 6/2009 | Judson et al. |
| 2009/0156953 A1 | 6/2009 | Wondka et al. |
| 2009/0165799 A1 | 7/2009 | Duquette et al. |
| 2009/0173347 A1 | 7/2009 | Berthon-Jones |
| 2009/0173349 A1 | 7/2009 | Hernandez et al. |
| 2009/0183739 A1 | 7/2009 | Wondka |
| 2009/0199855 A1 | 8/2009 | Davenport |
| 2009/0205662 A1 | 8/2009 | Kwok et al. |
| 2009/0241947 A1 | 10/2009 | Bedini et al. |
| 2009/0241951 A1 | 10/2009 | Jafari et al. |
| 2009/0250066 A1 | 10/2009 | Daly |
| 2009/0255533 A1 | 10/2009 | Freitag et al. |
| 2009/0260625 A1 | 10/2009 | Wondka |
| 2009/0277452 A1 | 11/2009 | Lubke et al. |
| 2009/0293877 A1 | 12/2009 | Blanch et al. |
| 2009/0301495 A1 | 12/2009 | Pierro et al. |
| 2009/0308395 A1 | 12/2009 | Lee et al. |
| 2009/0320851 A1 | 12/2009 | Selvarajan et al. |
| 2010/0043786 A1 | 2/2010 | Freitag et al. |
| 2010/0071697 A1 | 3/2010 | Jafari et al. |
| 2010/0083968 A1 | 4/2010 | Wondka et al. |
| 2010/0108073 A1 | 5/2010 | Zollinger et al. |
| 2010/0132716 A1 | 6/2010 | Selvarajan et al. |
| 2010/0132717 A1 | 6/2010 | Davidson et al. |
| 2010/0163043 A1 | 7/2010 | Hart et al. |
| 2010/0170512 A1 | 7/2010 | Kuypers et al. |

(56) References Cited

U.S. PATENT DOCUMENTS

| | | |
|---|---|---|
| 2010/0170513 A1 | 7/2010 | Bowditch et al. |
| 2010/0192957 A1 | 8/2010 | Hobson et al. |
| 2010/0218766 A1 | 9/2010 | Milne |
| 2010/0224196 A1 | 9/2010 | Jablons |
| 2010/0252037 A1 | 10/2010 | Wondka et al. |
| 2010/0252039 A1 | 10/2010 | Cipollone et al. |
| 2010/0252040 A1 | 10/2010 | Kapust et al. |
| 2010/0252041 A1 | 10/2010 | Kapust et al. |
| 2010/0252042 A1 | 10/2010 | Kapust et al. |
| 2010/0252043 A1 | 10/2010 | Freitag |
| 2010/0252044 A1 | 10/2010 | Duquette et al. |
| 2010/0269834 A1 | 10/2010 | Freitag et al. |
| 2010/0275920 A1 | 11/2010 | Tham et al. |
| 2010/0275921 A1 | 11/2010 | Schindhelm et al. |
| 2010/0282251 A1 | 11/2010 | Calluaud et al. |
| 2010/0282810 A1 | 11/2010 | Hawes |
| 2010/0288279 A1 | 11/2010 | Seiver et al. |
| 2010/0288289 A1 | 11/2010 | Nasir |
| 2010/0300445 A1 | 12/2010 | Chatburn et al. |
| 2010/0300446 A1 | 12/2010 | Nicolazzi et al. |
| 2010/0307487 A1 | 12/2010 | Dunsmore et al. |
| 2010/0307495 A1 | 12/2010 | Kepler et al. |
| 2010/0307499 A1 | 12/2010 | Eger et al. |
| 2010/0307500 A1 | 12/2010 | Armitstead |
| 2010/0307502 A1 | 12/2010 | Rummery et al. |
| 2010/0313891 A1 | 12/2010 | Veliss et al. |
| 2010/0313898 A1 | 12/2010 | Richard et al. |
| 2010/0319703 A1 | 12/2010 | Hayman et al. |
| 2010/0326441 A1 | 12/2010 | Zucker et al. |
| 2010/0326446 A1 | 12/2010 | Behlmaier |
| 2011/0000489 A1 | 1/2011 | Laksov et al. |
| 2011/0009763 A1 | 1/2011 | Levitsky et al. |
| 2011/0011402 A1 | 1/2011 | Berthon-Jones |
| 2011/0023878 A1 | 2/2011 | Thiessen |
| 2011/0023881 A1 | 2/2011 | Thiessen |
| 2011/0034819 A1 | 2/2011 | Desforges et al. |
| 2011/0036352 A1 | 2/2011 | Estes et al. |
| 2011/0041850 A1 | 2/2011 | Vandine et al. |
| 2011/0041855 A1 | 2/2011 | Gunaratnam et al. |
| 2011/0061647 A1 | 3/2011 | Stahmann et al. |
| 2011/0067704 A1 | 3/2011 | Kooij et al. |
| 2011/0067709 A1 | 3/2011 | Doshi et al. |
| 2011/0071444 A1 | 3/2011 | Kassatly et al. |
| 2011/0073107 A1 | 3/2011 | Rodman et al. |
| 2011/0073116 A1 | 3/2011 | Genger et al. |
| 2011/0087123 A9 | 4/2011 | Choncholas et al. |
| 2011/0088690 A1 | 4/2011 | Djupesland et al. |
| 2011/0094518 A1 | 4/2011 | Cipollone et al. |
| 2011/0100365 A1 | 5/2011 | Wedler et al. |
| 2011/0114098 A1 | 5/2011 | McAuley et al. |
| 2011/0125052 A1 | 5/2011 | Davenport et al. |
| 2011/0126841 A1 | 6/2011 | Matula, Jr. et al. |
| 2011/0132363 A1 | 6/2011 | Chalvignac |
| 2011/0139153 A1 | 6/2011 | Chalvignac |
| 2011/0146687 A1 | 6/2011 | Fukushima |
| 2011/0155140 A1 | 6/2011 | Ho et al. |
| 2011/0162650 A1 | 7/2011 | Miller et al. |
| 2011/0162655 A1 | 7/2011 | Gunaratnam et al. |
| 2011/0178419 A1 | 7/2011 | Wood et al. |
| 2011/0180068 A1 | 7/2011 | Kenyon et al. |
| 2011/0197885 A1 | 8/2011 | Wondka et al. |
| 2011/0209705 A1 | 9/2011 | Freitag |
| 2011/0214676 A1 | 9/2011 | Allum et al. |
| 2011/0220105 A1 | 9/2011 | Meier |
| 2011/0232642 A1 | 9/2011 | Bliss et al. |
| 2011/0247625 A1 | 10/2011 | Boussignac |
| 2011/0253147 A1 | 10/2011 | Gusky et al. |
| 2011/0259327 A1 | 10/2011 | Wondka et al. |
| 2011/0265796 A1 | 11/2011 | Amarasinghe et al. |
| 2011/0277765 A1 | 11/2011 | Christopher et al. |
| 2011/0284003 A1 | 11/2011 | Douglas et al. |

FOREIGN PATENT DOCUMENTS

| | | |
|---|---|---|
| DE | 19841070 | 5/2000 |
| DE | 19849571 | 5/2000 |
| DE | 10337138.9 | 3/2005 |
| DE | 10 2006 023 637.8 | 11/2007 |
| EP | 0125424 | 11/1984 |
| EP | 0692273 | 1/1996 |
| EP | 0778035 | 6/1997 |
| EP | 1359961 | 11/2003 |
| EP | 2377462 | 11/2010 |
| GB | 2174609 | 11/1986 |
| GB | 2201098 | 8/1988 |
| GB | 1055148 | 6/1989 |
| GB | 2338420 | 12/1999 |
| JP | S63-57060 | 3/1998 |
| JP | 2002-204830 | 7/2002 |
| WO | WO-92/11054 | 7/1992 |
| WO | WO-98/01176 | 1/1998 |
| WO | WO-99/04841 | 2/1999 |
| WO | WO-00/64521 | 11/2000 |
| WO | WO-01/76655 | 10/2001 |
| WO | WO-02/062413 | 8/2002 |
| WO | WO-2004/009169 | 1/2004 |
| WO | WO-2005/014091 | 2/2005 |
| WO | WO-2005/018524 | 3/2005 |
| WO | WO-2006/138580 | 12/2006 |
| WO | WO-2007/035804 | 3/2007 |
| WO | WO-2007/139531 | 12/2007 |
| WO | WO-2007142812 | 12/2007 |
| WO | WO-2008/014543 | 2/2008 |
| WO | WO-2008/019102 | 2/2008 |
| WO | WO-2008/052534 | 5/2008 |
| WO | WO-2008/112474 | 9/2008 |
| WO | WO-2008/138040 | 11/2008 |
| WO | WO-2008/144589 | 11/2008 |
| WO | WO-2008/144669 | 11/2008 |
| WO | WO-2009/042973 | 4/2009 |
| WO | WO-2009/042974 | 4/2009 |
| WO | WO-2009/059353 | 5/2009 |
| WO | WO-2009/064202 | 5/2009 |
| WO | WO-2009/074160 | 6/2009 |
| WO | WO-2009/082295 | 7/2009 |
| WO | WO-2009/087607 | 7/2009 |
| WO | WO-2009/092057 | 7/2009 |
| WO | WO-2009/103288 | 8/2009 |
| WO | WO-2009/109005 | 9/2009 |
| WO | WO-2009/115944 | 9/2009 |
| WO | WO-2009/115948 | 9/2009 |
| WO | WO 2009/115949 | 9/2009 |
| WO | WO-2009/129506 | 10/2009 |
| WO | WO-2009/136101 | 11/2009 |
| WO | WO-2009/139647 | 11/2009 |
| WO | WO-2009/149351 | 12/2009 |
| WO | WO-2009/149353 | 12/2009 |
| WO | WO-2009/149355 | 12/2009 |
| WO | WO-2009/149357 | 12/2009 |
| WO | WO-2009/151344 | 12/2009 |
| WO | WO-2009/151791 | 12/2009 |
| WO | WO-2010/000135 | 1/2010 |
| WO | WO-2010/021556 | 2/2010 |
| WO | WO-2010/022363 | 2/2010 |
| WO | WO-2010/039989 | 4/2010 |
| WO | WO-2010/041966 | 4/2010 |
| WO | WO-2010/044034 | 4/2010 |
| WO | WO-2010/057268 | 5/2010 |
| WO | WO-2010/059049 | 5/2010 |
| WO | WO-2010/060422 | 6/2010 |
| WO | WO-2010/068356 | 6/2010 |
| WO | WO-2010/070493 | 6/2010 |
| WO | WO-2010/070497 | 6/2010 |
| WO | WO-2010/070498 | 6/2010 |
| WO | WO-2010/076711 | 7/2010 |
| WO | WO-2010/081223 | 7/2010 |
| WO | WO-2010/091157 | 8/2010 |
| WO | WO-2010/099375 | 9/2010 |
| WO | WO-2010/102094 | 9/2010 |
| WO | WO-2010/115166 | 10/2010 |
| WO | WO-2010/115168 | 10/2010 |

(56) References Cited

FOREIGN PATENT DOCUMENTS

| | | |
|---|---|---|
| WO | WO-2010/115169 | 10/2010 |
| WO | WO-2010/115170 | 10/2010 |
| WO | WO-2010/116275 | 10/2010 |
| WO | WO-2010/132853 | 11/2010 |
| WO | WO-2010/136923 | 12/2010 |
| WO | WO-2010/139014 | 12/2010 |
| WO | WO-2010/150187 | 12/2010 |
| WO | WO-2011/002608 | 1/2011 |
| WO | WO-2011/004274 | 1/2011 |
| WO | WO-2011/006184 | 1/2011 |
| WO | WO-2011/006199 | 1/2011 |
| WO | WO-2011/014931 | 2/2011 |
| WO | WO-2011/017033 | 2/2011 |
| WO | WO-2011/017738 | 2/2011 |
| WO | WO-2011/021978 | 2/2011 |
| WO | WO-2011/022779 | 3/2011 |
| WO | WO-2011/024383 | 3/2011 |
| WO | WO-2011/029073 | 3/2011 |
| WO | WO-2011/029074 | 3/2011 |
| WO | WO-2011/035373 | 3/2011 |
| WO | WO-2011/038950 | 4/2011 |
| WO | WO-2011/038951 | 4/2011 |
| WO | WO-2011/044627 | 4/2011 |
| WO | WO-2011/057362 | 5/2011 |
| WO | WO 2011/059346 | 5/2011 |
| WO | WO-2011/061648 | 5/2011 |
| WO | WO-2011/062510 | 5/2011 |
| WO | WO-2011/086437 | 7/2011 |
| WO | WO-2011/086438 | 7/2011 |
| WO | WO-2011/112807 | 9/2011 |

OTHER PUBLICATIONS

In the U.S. Patent and Trademark Office, Supplemental Notice of Allowance dated in re: U.S. Appl. No. 10/771,803, dated Nov. 7, 2008, 2 pages.
In the U.S. Patent and Trademark Office, Examiner's Interview Summary in re: U.S. Appl. No. 10/771,803, dated Oct. 31, 2008, 4 pages.
In the U.S. Patent and Trademark Office, Notice of Allowance dated in re: U.S. Appl. No. 10/771,803, dated Oct. 20, 2008, 8 pages.
In the U.S. Patent and Trademark Office, Examiner's Interview Summary in re: U.S. Appl. No. 10/771,803, dated Nov. 2, 2007, 2 pages.
In the U.S. Patent and Trademark Office, Office Action in re: U.S. Appl. No. 10/771,803, dated Jun. 14, 2007, 12 pages.
In the U.S. Patent and Trademark Office, Restriction Requirement in re: U.S. Appl. No. 12/271,484, dated Feb. 9, 2011, 5 pages.
In the U.S. Patent and Trademark Office, Restriction Requirement in re: U.S. Appl. No. 12/754,437, dated Aug. 16, 2011, 5 pages.
In the U.S. Patent and Trademark Office, Non-Final Office Action dated in re: U.S. Appl. No. 10/567,746, dated Oct. 5, 2009, 9 pages.
In the U.S. Patent and Trademark Office, Notice of Allowance and Examiner's Interview Summary in re: U.S. Appl. No. 11/523,519, dated Jan. 16, 2009, 10 pages.
In the U.S. Patent and Trademark Office, Examiner's Interview Summary in re: U.S. Appl. No. 11/523,519, dated Jan. 13, 2009, 4 pages.
In the U.S. Patent and Trademark Office, Final Office Action in re: U.S. Appl. No. 11/523,519, dated Jul. 11, 2008, 13 pages.
In the U.S. Patent and Trademark Office, Examiner's Interview Summary in re: U.S. Appl. No. 11/523,519, dated Apr. 10, 2008, 3 pages.
In the U.S. Patent and Trademark Office, Final Office Action in re: U.S. Appl. No. 11/523,519, dated Nov. 26, 2007, 14 pages.
In the U.S. Patent and Trademark Office, Office Action in re: U.S. Appl. No. 11/523,519, dated Mar. 7, 2007, 11 pages.
In the U.S. Patent and Trademark Office, Restriction Requirement in re: U.S. Appl. No. 11/523,518, dated Dec. 30, 2009, 4 pages.
In the U.S. Patent and Trademark Office, Supplemental Notice of Allowance in re: U.S. Appl. No. 11/798,965, dated Aug. 21, 2009, 4 pages.
In the U.S. Patent and Trademark Office, Notice of Allowance in re: U.S. Appl. No. 11/798,965, dated Jul. 17, 2009, 5 pages.
In the U.S. Patent and Trademark Office, Final Office Action in re: U.S. Appl. No. 11/798,965, dated Apr. 9, 2009, 6 pages.
In the U.S. Patent and Trademark Office, Office Action in re: U.S. Appl. No. 11/798,965, dated Jul. 29, 2008, 12 pages.
In the U.S. Patent and Trademark Office, Office Action in re: U.S. Appl. No. 12/578,283, dated Oct. 19, 2011, 5 pages.
In the U.S. Patent and Trademark Office, Restriction/Election Requirement in re: U.S. Appl. No. 11/882,530, dated Apr. 27, 2011, 5 pages.
In the U.S. Patent and Trademark Office, Supplemental Notice of Allowance in re: U.S. Appl. No. 10/870,849, dated Jun. 16, 2009, 2 pages.
In the U.S. Patent and Trademark Office, Notice of Allowance in re: U.S. Appl. No. 10/870,849, dated Jun. 3, 2009, 4 pages.
In the U.S. Patent and Trademark Office, Notice of Allowance in re: U.S. Appl. No. 10/870,849, dated May 14, 2009, 8 pages.
In the U.S. Patent and Trademark Office, Restriction in re: U.S. Appl. No. 10/870,849, dated Nov. 16, 2007, 5 pages.
In the U.S. Patent and Trademark Office, Examiner's Interview Summary in re: U.S. Appl. No. 10/870,849, dated Jul. 27, 2007, 2 pages.
In the U.S. Patent and Trademark Office, Office Action in re: U.S. Appl. No. 10/870,849, dated Feb. 22, 2007, 13 pages.
In the U.S. Patent and Trademark Office, Restriction/Election Requirement in re: U.S. Appl. No. 12/493,677, dated Aug. 5, 2011, 5 pages.
In the U.S. Patent and Trademark Office, Restriction/Election Requirement in re: U.S. Appl. No. 12/153,423, dated Oct. 6, 2011, 8 pages.
In the U.S. Patent and Trademark Office, Notice of Allowance in re: U.S. Appl. No. 10/922,054, dated Feb. 12, 2008, 6 pages.
In the U.S. Patent and Trademark Office, Final Office Action in re: U.S. Appl. No. 10/922,054, dated Nov. 27, 2007, 9 pages.
In the U.S. Patent and Trademark Office, Office Action in re: U.S. Appl. No. 10/922,054, dated Mar. 14, 2007, 14 pages.
In the U.S. Patent and Trademark Office, Office Action in re: U.S. Appl. No. 10/922,054, dated Sep. 7, 2006, 21 pages.
In the U.S. Patent and Trademark Office, Restriction Requirement in re: U.S. Appl. No. 10/922,054, dated May 17, 2006, 5 pages.
In the U.S. Patent and Trademark Office, Notice of Allowance and Examiner's Interview Summary in re: U.S. Appl. No. 12/076,062, dated Nov. 2, 2011, 8 pages.
In the U.S. Patent and Trademark Office, Office Action in re: U.S. Appl. No. 12/076,062, dated Jan. 13, 2011, 14 pages.
In the U.S. Patent and Trademark Office, Office Action in re: U.S. Appl. No. 12/355,753, dated Sep. 28, 2011, 32 pages.
In the U.S. Patent and Trademark Office, *Ex Parte Quayle* Office Action in re: U.S. Appl. No. 29/388,700, dated Oct. 7, 2011, 5 pages.
"AARC Clinical Practice Guideline: Oxygen Therapy in the Home or Extended Care Facility," *Resp. Care*, 1992: 37(8), pp. 918-922.
"ATS Statement: Guidelines for the Six-Minute Walk Test," *Am. J. Respir. Crit. Care Med.*, 2002: 166, pp. 111-117.
"Passy-Muir Speaking Valves," *Respiratory*, Nov. 13, 1998, 7 pages.
Ambrosino, "Exercise and noninvasive ventilatory support," *Monaldi Arch Chest Dis.*, 2000: 55(3): 242-246.
Ambrosino, "Weaning and Respiratory Muscle Dysfunction: The Egg Chicken Dilemma," *Chest*, 2005: 128(2), pp. 481-483.
Bach et al., "Intermittent Positive Pressure Ventilation via Nasal Access in The Management of Respiratory Insufficiency," *Chest*, 1987: 92(1), pp. 168-170.
Banner et al., "Extubating at a Pressure Support Ventilation Level Corresponding to Zero Imposed Work of Breathing," *Anesthesiology*, Sep. 1994: 81(3A), p. A271.
Banner et al., "Imposed Work of Breathing and Methods of Triggering a Demand-Flow, Continuous Positive Airway Pressure System," *Critical Care Medicine*, 1993: 21(2), pp. 183-190.
Banner et al., "Site of Pressure Measurement During Spontaneous Breathing with Continuous Positive Airway Pressure: Effect on Calculating Imposed Work of Breathing," *Critical Care Medicine*, 1992: 20(4), pp. 528-533.
Barakat et al., "Effect of noninvasive ventilatory support during exercise of a program in pulmonary rehabilitation in patients with COPD," *Int. J. Chron. Obstruct. Pulmon. Dis.*, 2007: 2(4), pp. 585-591.

(56) References Cited

OTHER PUBLICATIONS

Barreiro et al., "Noninvasive ventilation," Crit Care Clin., 2007; 23(2): 201-22.
Bauer et al., "ADAM Nasal CPAP Circuit Adaptation: A Case Report," Sleep, 1991: 14(3), pp. 272-273.
Blanch, "Clinical Studies of Tracheal Gas Insufflation," Resp. Care, 2001: 45(2), pp. 158-166.
Borghi-Silva et al., "Non-invasive ventilation improves peripheral oxygen saturation and reduces fatigability of quadriceps in patients with COPD," Respirology, 2009, 14:537-546.
Bossi et al., "Continuous Positive Airway Pressure in the Spontaneously Breathing Newborn by Means of Bilateral Nasal Cannulation," Monatsschr Kinderheilkd, 1975: 123(4), pp. 141-146.
Boussarsar et al., "Relationship between ventilatory settings and barotrauma in the acute respiratory distress syndrome," Intensive Care Med., 2002: 28(4): 406-13.
Chang et al., "Reduced Inspiratory Muscle Endurance Following Successful Weaning From Prolonged Mechanical Ventilation," Chest, 2005: 128(2), pp. 553-559.
Charlotte Regional Medical Center, "Application of the Passy-Muir Tracheostomy and Ventilator," Speech-Language Pathology Department, Jan. 1995, 8 pages.
Christopher et al., "Preliminary Observations of Transtracheal Augmented Ventilation for Chronic Severe Respiratory Disease," Resp. Care, 2001: 46(1), pp. 15-25.
Christopher, et al., "Transtracheal Oxygen Therapy for Refractory Hypoxemia," JAMA, 1986: 256(4), pp. 494-497.
Ciccolella et al.; "Administration of High-Flow, Vapor-phased, Humidified Nasal Cannula Air (HF-HNC) Decreases Work of Breathing (WOB) in Healthy Subjects During Exercise," AmJRCCM, Apr. 2001: 163(5), Part 2, pp. A622. (Abstract Only).
Clini et al., "The Italian multicentre study on noninvasive ventilation in chronic obstructive pulmonary disease patients," Eur. Respir. J., 2002, 20(3): 529-538.
Costa et al., "Influence of noninvasive ventilation by BiPAP® on exercise tolerance and respiratory muscle strength in chronic obstructive pulmonary disease patients (COPD)," Rev. Lat. Am. Enfermagem., 2006: 14(3), pp. 378-382.
Díaz et al., "Breathing Pattern and Gas Exchange at Peak Exercise in COPD Patients With and Without Tidal Flow Limitation at Rest," European Respiratory Journal, 2001: 17, pp. 1120-1127.
Enright, "The six-minute walk test," Resp. Care, 2003: 8, pp. 783-785.
Ferreira et al., "Trigger Performance of Mid-level ICU Mechanical Ventilators During Assisted Ventilation: A Bench Study," Intensive Care Medicine, 2008,34:1669-1675.
Fink, "Helium-Oxygen: An Old Therapy Creates New Interest," J. Resp. Care. Pract. now RT for Decision Makers in Respiratory Care, 1999, pp. 71-76.
Gaughan et al., "A Comparison in a Lung Model of Low- and High-Flow Regulators for Transtracheal Jet Ventilation," Anesthesiology, 1992: 77(1), pp. 189-199.
Gregoretti, et al., "Transtracheal Open Ventilation in Acute Respiratory Failure Secondary to Severe Chronic Obstructive Pulmonary Disease Exacerbation," Am. J. Resp. Crit. Care. Med., 2006: 173(8), pp. 877-881.
Haenel et al., "Efficacy of Selective Intrabronchial Air Insufflation in Acute Lobar Colapse," Am. J. Surg., 1992: 164(5), pp. 501-505.
Keilty et al., "Effect of inspiratory pressure support on exercise tolerance and breathlessness in patients with severe stable chronic obstructive pulmonary disease," Thorax, 1994, 49(10): 990-994.
Köhnlein et al., "Noninvasive ventilation in pulmonary rehabilitation of COPD patients," Respir. Med., 2009, 103: 1329-1336.
Koska et al., "Evaluation of a Fiberoptic System for Airway Pressure Monitoring," J. Clin. Monit., 1993: 10(4), pp. 247-250.
Lewis, "Breathless No More, Defeating Adult Sleep Apnea," FDA Consumer Magazine, Jun. 1992, pp. 33-37.
Limberg et al., "Changes in Supplemental Oxygen Prescription in Pulmonary Rehabilitation," Resp. Care, 2006:51(11), p. 1302.

Macinryre, "Long-Term Oxygen Therapy: Conference Summary," Resp. Care, 2000: 45(2), pp. 237-245.
Macintyre et al., "Acute exacerbations and repiratory failure in chronic obstructive pulmonary disease," Proc. Am. Thorac. Soc., 2008: 5(4), pp. 530-535.
Massie et al., "Clinical Outcomes Related to Interface Type in Patients With Obstructive Sleep Apnea/Hypopnea Syndrome Who are Using Continuous Positive Airway Pressure," Chest, 2003: 123(4), pp. 1112-1118.
McCoy, "Oxygen Conservation Techniques and Devices," Resp. Care, 2000: 45(1), pp. 95-104.
McGinley, "A nasal cannula can be used to treat obstructive sleep apnea"; Am. J. Resp. Crit. Care Med., 2007: 176(2), pp. 194-200.
Menadue et al., "Non-invasive ventilation during arm exercise and ground walking in patients with chronic hypercapnic respiratory failure," Respirology, 2009, 14(2): 251-259.
Menon et al., "Tracheal Perforation. A Complication Associated with Transtracheal Oxygen Therapy," Chest, 1993: 104(2), pp. 636-637.
Messinger et al., "Using Tracheal Pressure to Trigger the Ventilator and Control Airway Pressure During Continuous Positive Airway Pressure Decreases Work of Breathing," Chest, 1995: vol. 108(2), pp. 509-514.
Mettey, "Use of CPAP Nasal Cannula for Aids of the Newborns in Tropical Countries," Medecine Tropicale, 1985: 45(1), pp. 87-90.
Nahmias et al., "Treatment of the Obstructive Sleep Apnea Syndrome Using a Nasopharyngeal Tube", Chest, 1988:94(6), pp. 1142-1147.
Nava et al., "Non-invasive ventilation," Minerva Anestesiol., 2009: 75(1-2), pp. 31-36.
Passy-Muir Inc., "Clinical Inservice Outline", Apr. 2004, 19 pages.
Peters et al., "Combined Physiological Effects of Bronchodilators and Hyperoxia on Exertional Dyspnea in Normoxic COPD," Thorax, 2006: 61, pp. 559-567.
Polkey et al., "Inspiratory pressure support reduces slowing of inspiratory muscle relations rate during exhaustive treadmill walking in sever COPD," Am. J. Resp. Crit. Care Med., 1996: 154(4, 10), pp. 1146-1150.
Porta et al., "Mask proportional assist vs pressure support ventilation in patients in clinically stable condition with chronic venilatory failure," Chest, 2002: 122(2), pp. 479-488.
Prigent et al., "Comparative Effects of Two Ventilatory Modes on Speech in Tracheostomized Patients with Neuromuscular Disease," Am. J. Resp. Crit. Care Med., 2003: 167(8), pp. 114-119.
Puente-Maestu et al., "Dyspnea, Ventilatory Pattern, and Changes in Dynamic Hyperinflation Related to the Intensity of Constant Work Rate Exercise in COPD," Chest, 2005: 128(2), pp. 651-656.
Ram et al., "Non-invasive positive pressure ventilation for treatment of respiratory failure due to exacerbations of chroic obstructive pulmonary disease," Cochrane Database Syst Rev., 2004(3):1-72.
Rothe et al., "Near Fatal Complication of Transtracheal Oxygen Therapy with the SCOOP(R) System," Pneumologie, 1996: 50(10), pp. 700-702. (English Abstract provided.).
Rothfleisch et al., "Facilitation of fiberoptic nasotracheal intubation in a morbidly obese patient by simultaneous use of nasal CPAP," Chest, 1994, 106(1): 287-288.
Sanders et al., "CPAP Via Nasal Mask: A Treatment for Occlusive Sleep Apnea," Chest, 1983: 83(1), pp. 144-145.
Sinderby et al., "Neural control of mechanical ventilation in respiratory failure," Nat. Med., 1999: 5(12), pp. 1433-1436.
Somfay et al., "Dose-Response Effect of Oxygen on Hyperinflation and Exercise Endurance in Nonhypoxaemic COPD Patients," Eur. Resp. J., 2001: 18, pp. 77-84.
Sullivan et al., "Reversal of Obstructive Sleep Apnoea by Continuous Positive Airway Pressure Applied Through the Nares," The Lancet, 1981: 1(8225), pp. 862-865.
Sullivan, "Home treatment of obstructive sleep apnoea with continuous positive airway pressure applied through a nose-mask," Bull Eur Physiopathol Respir., 1984: 20(1), pp. 49-54.
Tiep et al., "Pulsed nasal and transtracheal oxygen delivery," Chest, 1990: 97, pp. 364-368.
Tsuboi et al., "Ventilatory Support During Exercise in Patients With Pulmonary Tuberculosis Sequelae," Chest, 1997: 112(4), pp. 1000-1007.

(56) References Cited

OTHER PUBLICATIONS

*VHA/DOD Clinical Practice Guideline*, "Management of Chronic Obstructive Pulmonary Disease," Aug. 1999, Ver. 1.1a, Updated Nov. 1999.

Wijkstra et al., "Nocturnal non-invasive positive pressure ventilation for stable chronic obstructive pulmonary disease," *Cochrane Database Syst. Rev.*, 2002, 3: 1-22.

Yaeger et al., "Oxygen Therapy Using Pulse and Continuous Flow With a Transtracheal Catheter and a Nasal Cannula," *Chest*, 1994: 106, pp. 854-860.

Walsh, "McGraw Hill Pocket reference Machinists' and Metalworker' Pocket Reference," *New York McGraw-Hill*, 2000, pp. 3-67, submitting 3 pages.

International Preliminary Report and Written Opinion on Patentability for PCT/DE2004/001646, dated Jul. 3, 2006.

European patent Office Search Report issued Oct. 19, 2007 in co-pending EP 04762494.

International Search Report and Written Opinion for PCT/US04/26800 issued Jun. 22, 2006.

International Search Report and Written Opinion for PCT/US07/12108, dated Aug. 8, 2008.

International Search Report and Written Opinion for PCT/US07/17400, dated Apr. 28, 2008.

International Search Report and Written Opinion for PCT/US08/64015, dated Sep. 26, 2008.

International Search Report and Written Opinion for PCT/US08/64164, dated Sep. 29, 2008.

International Search Report and Written Opinion for PCT/US08/78031, dated Nov. 24, 2008.

International Search Report and Written Opinion for PCT/US08/78033, dated Dec. 3, 2008.

International Search Report and Written Opinion for PCT/US09/054673, dated Oct. 8, 2009.

International Search Report and Written Opinion for PCT/US09/41027, dated Dec. 14, 2009.

International Search Report and Written Opinion for PCT/US09/59272, dated Dec. 2, 2009.

International Search Report and Written Opinion for PCT/US2006/036600, dated Apr. 3, 2007.

International Search Report and Written Opinion for PCT/US2009/031355 issued Mar. 11, 2009.

International Search Report and Written Opinion for PCT/US2009/041034, dated Jun. 10, 2009.

International Search Report and Written Opinion for PCT/US2010/029871, dated Jul. 12, 2010.

International Search Report and Written Opinion for PCT/US2010/029873, dated Jun. 28, 2010.

International Search Report and Written Opinion for PCT/US2010/029874, dated Jul. 12, 2010.

International Search Report and Written Opinion for PCT/US2010/029875, dated Jul. 12, 2010.

International Search Report and Written Opinion for PCT/US2010/047920, dated Nov. 1, 2010.

International Search Report and Written Opinion for PCT/US2010/047921, dated Jan. 27, 2011.

International Search Report for PCT/DE2004/001646, dated Jan. 17, 2005.

\* cited by examiner $$G_i = G_{si} + G_v + G_e + G_{sa}$$

To Ventilator

To Ventilator

To Ventilator

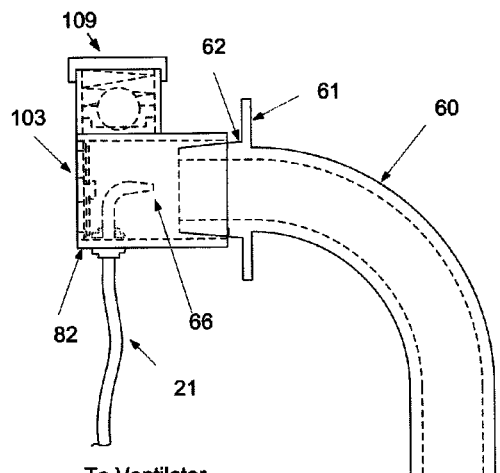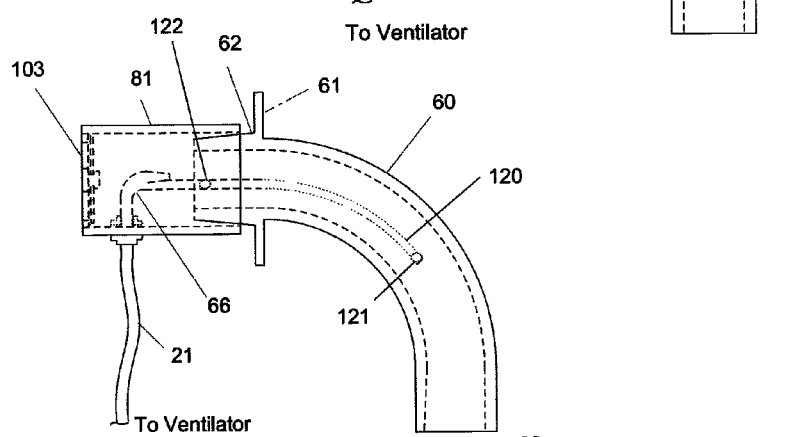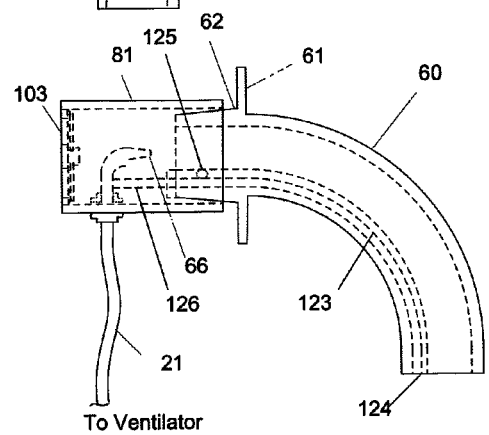

Detail B

Section A-A

Section A-A

To Ventilator

To Ventilator

To Ventilator

METHODS AND DEVICES FOR PROVIDING MECHANICAL VENTILATION WITH AN OPEN AIRWAY INTERFACE

PRIORITY APPLICATIONS

This application claims priority to U.S. Provisional Patent Application Ser. No. 61/091,198, filed Aug. 22, 2008 and U.S. Provisional Patent Application Ser. No. 61/136,269, filed Aug. 22, 2008; the disclosures of which are hereby incorporated by reference in their entireties.

CROSS-REFERENCE TO RELATED APPLICATIONS

This application further incorporates by reference in their entireties: U.S. Non-Provisional patent application Ser. No. 10/771,803 (U.S. Printed Publication 2005/0034721), filed Feb. 4, 2004, U.S. Non-Provisional patent application Ser. No. 10/870,849 (U.S. Printed Publication 2005/0005936), filed Jun. 17, 2004, and U.S. Non-Provisional patent application Ser. No. 12/239,723 (U.S. Printed Publication 2009/0151724), filed Sep. 26, 2008.

FIELD OF THE INVENTION

The present invention relates to ventilation therapy for persons suffering from respiratory impairment and breathing disorders, such as chronic obstructive pulmonary disease (COPD), pulmonary fibrosis, acute respiratory distress syndrome (ARDS), neuromuscular impairment, sleep apnea, influenza, various forms of mass casualty, and military use, and/or other breathing and airway impairments. More specifically, the present invention relates to providing mechanical respiratory support to a patient in an open airway ventilation system.

BACKGROUND OF THE INVENTION

There are two general types of mechanical ventilation control modes. A first type delivers gas to a patient based on a frequency selected by the clinician which is independent of patient activity. This type of ventilation, known as controlled mechanical ventilation, is used when the ventilator is needed to breathe for the patient such as when the patient is non-alert, sedated, unresponsive or paralyzed. A second type of ventilation, known as assisted mechanical ventilation, or assisted ventilation, or augmented ventilation, delivers gas to the patient in response to an inspiratory effort generated by the patient. This type of ventilation helps the patient breathe, such as when the patient has respiratory insufficiency such as COPD. There are also ventilators and modes of ventilation that combine the two modes of ventilation described above.

In the use of all ventilators a gas delivery circuit is required to deliver the gas from the ventilator to the patient. Also required is a ventilation patient interface which is in communication with the patient's airway. The gas delivery circuit connects to the patient interface so that the ventilator can deliver air into the patient's airway through the gas delivery circuit and through the patient interface. These interfaces can be non-invasive such as a mask over the nose and/or mouth or a nasal cannula, or can be invasive, such as an endotracheal tube, tracheostomy tube, or transtracheal catheter which is placed into the airway of the patient.

In a more specific case of respiratory support ventilation, the patient receives gas from the ventilator with a patient interface configuration known as an "open airway" system, meaning the patient's respiratory tract is open to atmosphere through their normal upper airway breathing routes (mouth and nose). Open airway ventilation (OAV) when used is typically used with spontaneously breathing patients who need respiratory support; however, OAV can also be used for ventilator dependent patients who cannot breathe. In the former case, the patient may be breathing "spontaneously" or naturally through their upper airway but their breathing is augmented by receiving additional gas from the ventilator through the "open" patient interface. The goal of this therapy is to help the patient's work of breathing with an OAV system, such that the patient is not encumbered with the various problems, limitations, obtrusiveness and side effects of closed airway positive pressure ventilation. This system is described in U.S. Pat. No. 7,487,778 (Freitag) and US Printed Publication 2005/0005936 (Wondka). The ventilation interface described in this prior art is typically a transtracheal ventilation catheter that is placed percutaneously through the patient's neck into the tracheal lumen, or a catheter placed into an existing airway tube, such as an uncuffed tracheostomy tube. Alternatively, the ventilation catheter is placed into a stent or stoma guide, such as a Montgomery T-Tube, or an endotracheal tube, or an airway prosthesis. In OAV, providing mechanical ventilation support to the lungs is not obviously possible, because air delivered from the ventilator has the potential of leaking out of the upper airway if the airway is open, thus rendering the system ineffective and limiting the additive volume that can be delivered to the lung. Therefore, special airflow delivery fluid dynamics are required to make the system efficacious and efficient, and special delivery systems and interface designs are required to accomplish these dynamics.

SUMMARY OF THE INVENTION

The present invention may be directed to methods and systems for providing ventilation mechanical support in an open airway ventilation system. In an embodiment of the present invention, a ventilation system may include a ventilator for supplying ventilation gas. A patient interface may include distal end in communication with a patient airway, a proximal end in communication with ambient air, and an airflow channel between the distal end and the proximal end. A gas delivery circuit may be adapted to attach to the patient interface without occluding the patient interface to allow ambient air to flow from outside the patient interface to the patient airway. The ventilation gas may entrain air from ambient and from the patient airway.

In another embodiment of the present invention, a ventilation system may include a ventilator for supplying ventilation gas. A patient interface may include distal end in communication with a patient airway, a proximal end in communication with ambient air, and an airflow channel between the distal end and the proximal end. A gas delivery circuit may be adapted to attach to the patient interface without occluding the patient interface to allow ambient air to flow from outside the patient interface to the patient airway. The gas delivery circuit may include a nozzle on a distal end of the gas delivery circuit, and wherein the nozzle is positioned outside the patient interface when supplying ventilation gas.

In another embodiment of the present invention, a ventilation system may include a ventilator for supplying ventilation gas. A patient interface may include distal end in communication with a patient airway, a proximal end in communication with ambient air, and an airflow channel between the distal end and the proximal end. The distal end may include one or more fenestrations. A gas delivery circuit may be adapted to attach to the patient interface without occluding the patient interface to allow ambient air to flow from outside the patient interface to the patient airway. The gas delivery circuit may include a nozzle located within the patient interface where the nozzle is positioned in proximity to the one or more fenestrations when supplying ventilation gas.

Embodiments of the present invention may include a ventilation system including a ventilator, a gas delivery circuit and a patient interface, the patient interface including a distal end in communication with a patient airway and a proximal end in communication with ambient air, wherein the gas delivery circuit is adapted to attach to the patient interface without occluding the patient interface to allow ambient air to flow from outside the interface into the patient airway, and wherein the gas delivery circuit is adapted to deliver the ventilator gas into the patient airway through the patient interface. Embodiments of the present invention may also include a ventilation system including a ventilator, a gas delivery circuit, and a patient interface, wherein the patient interface includes a distal end and a proximal end and an airflow channel extending from the proximal end to the distal end, wherein the distal end is in communication with a patient airway, and wherein the proximal end is in communication with ambient air, and wherein: (a) the gas delivery circuit includes a first end connected to the ventilator and a second end connected to the patient interface, and wherein the second end connection to the patient interface does not occlude the airflow channel such that ambient air can flow through the airflow channel into the airway; and (b) wherein the gas delivery circuit delivers gas from the ventilator to the patient airway. Embodiments of the present invention may also include a ventilation system including a ventilator, a gas delivery circuit, and a patient interface, wherein the patient interface includes a distal end and a proximal end and a airflow channel extending from the proximal end to the distal end, wherein the distal end is in communication with a patient airway, and wherein the proximal end is in communication with ambient air, and wherein: (a) the gas delivery circuit includes a first end connected to the ventilator and a second end connected to the patient interface, and wherein the second end connection to the patient interface does not occlude the airflow channel such that ambient air can flow through the airflow channel into the airway, and lung air can flow out of the airflow channel to ambient air; and (b) wherein the gas delivery circuit delivers gas from the ventilator to the patient airway. Embodiments of the present invention may also include a ventilation system including a ventilator and a gas delivery circuit, wherein the gas delivery circuit includes a first end adapted to connect to the ventilator and a second end including a connector adapted to connect to a ventilation patient interface, wherein the second end connector is adapted to connect to the ventilation patient interface so the ventilation patient interface maintains an open channel such that the open channel allows ambient air to flow from ambient through the patient interface into an airway.

Embodiments of the present invention may also include that the ventilator gas is delivered as a volume synchronized with the patient's inspiratory cycle, in which the volume is selected by the user. The ventilator gas may be delivered continuously, cyclically at a rate determined by the ventilator, as a volume cyclically synchronized with the patients breathing, and with a back up rate to deliver a mandatory number of breaths over a period of time, or as a volume cyclically during an inspiratory cycle to reduce the work of breathing, and during an expiratory cycle to create PEEP. The system may be used to treat a lung disease, a breathing disorder, or a neuromuscular disorder. The system may be used with a portable gas supply and used to enhance mobility. The patient interface may be an airway tube, tracheostomy tube, a T-tube, and stomal stent, a stoma, an endotracheal tube, a trans-cricothryoid tube, a trans-laryngectomy tube, a mask, a nasal mask, an oral mask, a nasal-oral mask, a cannula, a transtracheal cannula, a nasal cannula, an oral cannula, or a nasal-pharyngeal cannula.

Embodiments of the present invention may include those where the second end of the gas delivery circuit includes two gas delivery exit ports, and wherein the ventilation patient interface includes a left and right nasal cannula; where the second end of the gas delivery circuit includes a distal tip, wherein the distal tip includes a gas delivery nozzle and is adapted to locate the gas delivery nozzle between a distal end and proximal end of the ventilation patient interface; where the gas delivery circuit distal tip coplanar with entrance of the airway tube; where the gas delivery circuit distal tip is outside of entrance to airway tube; where the gas delivery circuit distal tip is coplanar with transition from straight section to curved section; where the gas delivery circuit connection to the patient interface includes an adjustment to adjust the position of the distal tip of the nozzle.

In certain embodiments, the patient interface may be an airway tube and the airway tube includes a fenestration and the gas delivery circuit distal tip is located near the fenestration; the gas delivery circuit distal tip is low profile, nozzle is side port in gas delivery circuit distal tip; the gas delivery circuit distal tip is angled to point toward distal end opening of airway tube; the gas delivery circuit distal end attaches to patient interface with an elbow connector; the gas delivery circuit distal end attaches to patient interface with an T-shaped connector; the gas delivery circuit distal end attaches to patient interface with an L-shaped connector; the gas delivery circuit distal end attaches to patient interface with an swivel connector; the gas delivery circuit distal attaches to patient interface with a connector which includes a one-way inspiratory valve allowing air flow in the inspired direction; the gas delivery circuit distal end attaches to patient interface with a connector which includes a one-way expiratory valve allowing air flow in the exhaled direction; the gas delivery circuit distal end connection to the patient interface includes a PEEP valve; the gas delivery circuit distal end connection to the patient interface includes a PEEP valve wherein the PEEP valve includes an adjustment; the gas delivery circuit distal end connection to the patient interface includes a PEEP valve wherein the PEEP valve setting is controlled by a pressure signal provided by the ventilator; the gas delivery circuit distal end connection to the patient interface includes an Inspiratory and Expiratory valve; the gas delivery circuit distal end connection to the patient interface includes an Inspiratory and PEEP valve; the gas delivery circuit distal end connection to the patient interface includes a baffle connection; the gas delivery circuit distal end connection to the patient interface includes a Heat moisture exchanger; the gas delivery circuit distal end connection to the patient interface includes a connector with a HME, inspiratory valve, and PEEP valve; the gas delivery circuit distal end connection to the patient interface includes a connector with a side connector; the gas delivery circuit distal end connection to the patient interface includes a connector with two side connectors; the gas delivery circuit distal end connection connects to the inside of the patient interface; or the gas delivery circuit distal end nozzle includes a tapered ID where the tapered ID restricts the ID from a larger dimension to a smaller dimension at the nozzle distal tip.

In certain embodiments, the ventilator gas exits the gas delivery circuit distal end as a Jet, with an exit speed of 50-350 meters per second; the ventilator gas exits the gas delivery circuit distal end as a jet, which entrains ambient air from outside the connector, where the entrainment is 25-300% of the ventilator gas.

In certain embodiments, the system includes sensors to measure the amount of air entrainment, and a control unit to adjust and regulating the amount of entrainment. The system may include humidity delivery, a humidification lumen, or a humidified gas delivery attachment. The gas delivery circuit distal end may include a breath sensor, which may be a breath sensor is a pressure sensing line included of a sensing lumen and sensing port; a sensing port orthogonal to air flow path facing distal direction; a sensing port orthogonal to air flow path facing proximal direction; sensing port parallel with gas flow path; a thermal flow sensor; an airway pressure sensing extension line adapted to extend a distance into the airway tube; an airway pressure sensing channel, and wherein the gas delivery circuit includes sensing connector to connect to the patient interface sensing channel; or a ventilation gas delivery channel, a pressure sensing channel, a humidification delivery channel, an oxygen bleed delivery channel, an oxygen and CO2 sensing channel, and a thermal sensor wire channel.

Embodiments may include those where the ventilation gas is air and oxygen is bled into the airway tube; the ventilation gas is oxygen; the ventilation gas is blended air and oxygen; or an oxygen sensing mechanism; a CO2 sensing mechanism. In certain embodiments the ventilator is adapted to vary the gas output parameters to achieve a desired FIO2; the ventilator is adapted to vary the gas output parameters to achieve a desired airway pressure; the ventilator is adapted to vary the gas output parameters to achieve a desired lung volume; the ventilator is adapted to vary the gas output parameters to achieve a desired inspiratory flow rate; a therapeutic gas is bled into the patient interface, such as helium, NO, HeliOx; output titration algorithms, to adjust the delivery of volume based on patient activity level using biofeedback, such as respiratory rate, inspiratory strength, I:E ratio, exhaled gas composition; output triggering algorithms, to adjust the timing of the delivery of volume based on patient comfort and activity level using biofeedback, such as respiratory rate, inspiratory strength, I:E ratio, exhaled gas composition; delivering blended air and oxygen and wherein the ventilator includes a blender, an external oxygen and air supply, and an external compressor; delivering blended air and oxygen and wherein the ventilator includes a blender, an external oxygen and air supply, and an internal compressor; or delivering blended air and oxygen and wherein the ventilator includes a blender, an external oxygen supply wherein the external oxygen supply is selected from the group of compressed oxygen gas, liquid oxygen or an oxygen concentrator, and an internal compressor, a gas analyzer, a humidifier unit, a microprocessor control system, and a lung volume sensor.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTIONS OF THE FIGURES

The accompanying drawings, which are included to provide a further understanding of the invention and are incorporated in and constitute a part of this specification, illustrate preferred embodiments of the invention and together with the detailed description serve to explain the principles of the invention. In the drawings:

FIG. 20 shows a gas delivery circuit connected to an airway tube with an open elbow connection, with a PEEP or exhalation valve attached to the side connection and an inspiratory valve.

FIG. 21 shows a gas delivery circuit connected to an airway tube with an open adaptor and with an extension tube for airway breath sensing and pressure sensing.

FIG. 22 shows a gas delivery circuit connected to an airway tube with an open adaptor where the airway tube has an airway sensing channel, and the circuit has a connection to attach to the sensing channel.

DETAILED DESCRIPTION OF THE PREFERRED EMBODIMENTS

In some cases, special airflow delivery fluid dynamics can be created by special drive pressures and escape velocities of the ventilation gas, and in other cases the special airflow delivery fluid dynamics can be created by special patient interface configurations. Embodiments of the present invention may include special patient interface configurations and geometries that optimize the efficacy of open system augmented ventilation.

Figure 1:
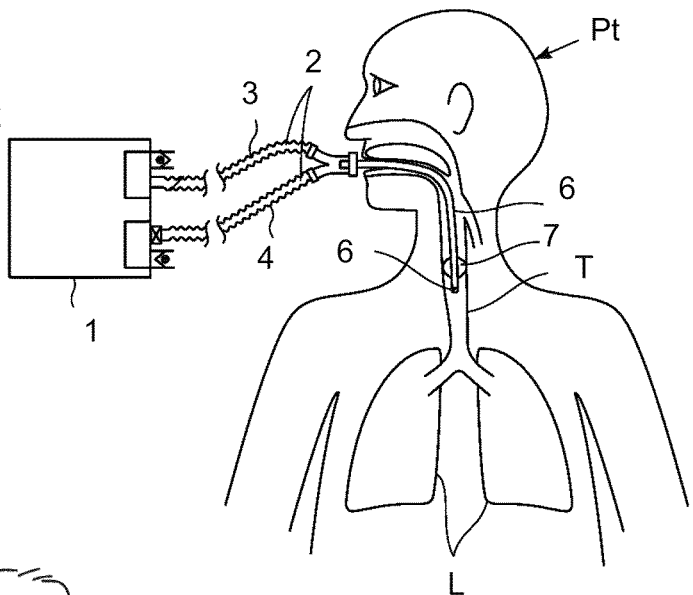
FIG. 1 shows a prior art conventional closed airway ventilation system, using a cuffed endotracheal tube.

FIG. 1 describes a conventional ventilation system, known as controlled mechanical ventilation (CMV) in which a ventilator 1 is connected to a patient Pt with a dual limb gas delivery circuit 2 and delivers gas to the patient Pt via an inspiratory limb 3 and gas is exhaled from lungs L back to the ventilator 1 through an expiratory limb 4. A typical patient ventilation interface is an endotracheal tube 6 with a cuff 7 within a trachea T such that the patient's lung L is closed off from ambient air, and is only connected to an air source through the ventilator gas delivery circuit 2. Air is forced into the lung L and the ventilator 1 can increase lung volume because it is a closed system, which is not open to ambient.

Figure 2:
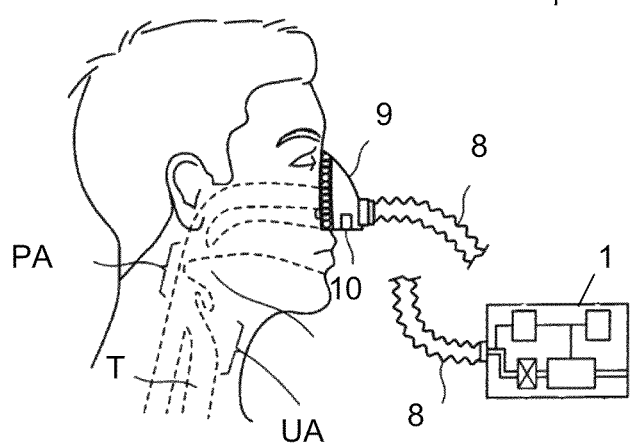
FIG. 2 shows a conventional non-invasive ventilation system using a sealing nasal mask.

FIG. 2 describes a conventional ventilation system, typically referred to as a Continuous Positive Airway Pressure (CPAP) system. There is a single limb gas delivery circuit 8 in this case through which the patient inhales and exhales. This system is also a closed ventilation system in that the patient ventilation interface is typically a non-invasive ventilation mask 9 (known as a non-invasive ventilation (NIV) mask), which is sealed against the patient's face so that the respiratory system is closed to ambient air. The non-invasive ventilation mask may include one or more mask exhaust ports 10. In this system the patient is spontaneously breathing, but spontaneously breathing from the gas supply supplied by the ventilator 1. Volume is forced into the lung and the ventilator 1 can increase lung volume because the system is a closed system, not connected to ambient. Airflow may pass through an upper airway UA and/or the oropharyngeal airway PA.

Figure 3:
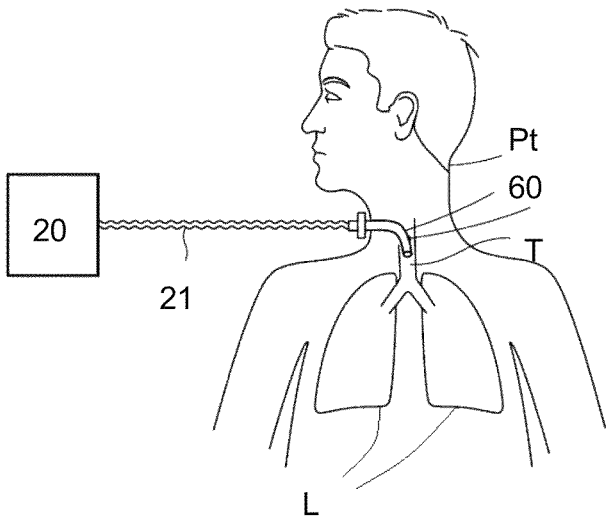
FIG. 3 shows an overview of an open airway ventilation system of the present invention with an open airway patient interface.

FIG. 3 describes an overview of an exemplary open ventilation system of the present invention in which the patient is inspiring and exhaling naturally through their upper airway. A patient ventilation interface may be a tracheostomy tube, or transtracheal catheter, which is typically connected to a ventilator 20 with a single limb gas delivery circuit 21. The single limb gas delivery circuit 21 may couple to an airway tube 60. An airway tube 60 may be various types of structures, including, but not limited to trach tubes, masks, cannulas, etc. The ventilator 20 in this case may provide ventilation assistance, or augmented ventilation to the patient. If the breathing circuit is large enough the patient can partially exhale through the breathing circuit, or if not, the patient exhales completely through the upper airway.

An open ventilation system is described by Freitag in US Patent Application No. 2005/0003472 and by Wondka in US Patent Application No. 2005/0005936. In these references, the breathing circuit is small for reasons of un-obtrusiveness and convenience to the user, or because of other performance factors such as gas delivery dynamics, and hence the patient exhales completely through their natural breathing route (upper airway), and only receives augmented ventilation through the breathing circuit. Due to special ventilator driving pressures and gas exit fluid dynamics out of the catheter, the ventilator has the potential of increasing lung volume or pressure despite the fact that it is an open upper airway system. Standard gas delivery techniques, such as with oxygen therapy, the lung volume and pressure would not be affected.

Figure 4:
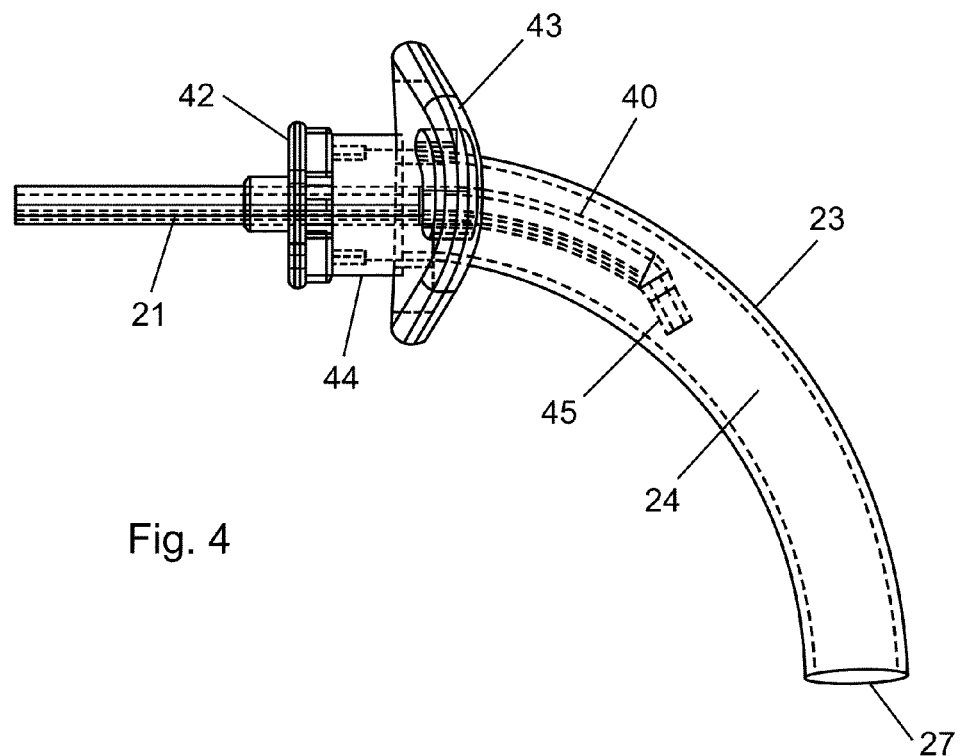
FIG. 4 shows a gas delivery circuit with a ventilation catheter placed into a trach tube patient interface with an open connection, with the ventilation catheter extending part way into the trach tube.

FIG. 4 describes a side view of a tracheostomy tube 23 and ventilation catheter 40 combination in which the connection between the ventilation catheter 40 and the trach tube 23 is open at the trach tube proximal end, and in which the catheter distal tip 45 is placed at a location near the mid length of the trach tube 23. This configuration may provide an increase in entrained airflow from ambient air through the trach tube opening. This configuration may enhance entrainment by resembling features of a jet pump. The section of trach tube distal to the catheter tip may be known as the nozzle of a jet pump, and the section proximal to the catheter tip (including the volume inside the trach tube proximal connector and ambient air volume directly outside the trach tube connector)

may be considered the vacuum chamber of the jet pump, from which the catheter exit gas entrains the volume. The ventilation catheter 40 can be pre-formed to match with the curvature of the trach tube 23, or can be shaped to be in contact with the superior surface of the inside of the trach tube, or can be shaped to be in contact with the inferior surface of the inside of the trach tube. The distal tip of the ventilation catheter 40 can be angulated to direct the jet exiting the nozzle through a trach tube airflow channel 24 and toward the distal tip 27 opening of the trach tube 23, which is essential in optimizing the jet performance of the system. The ventilation catheter 40 can also be shaped to be in contact with one of the lateral walls of the trach tube 23. The single limb gas delivery channel 21 may be coupled to the trach tube 23 using an airway tube connector 42 in communication with a connector 44, preferably a 15 mm connector, which is also in communication with a trach tube flange 43.

Figure 5:
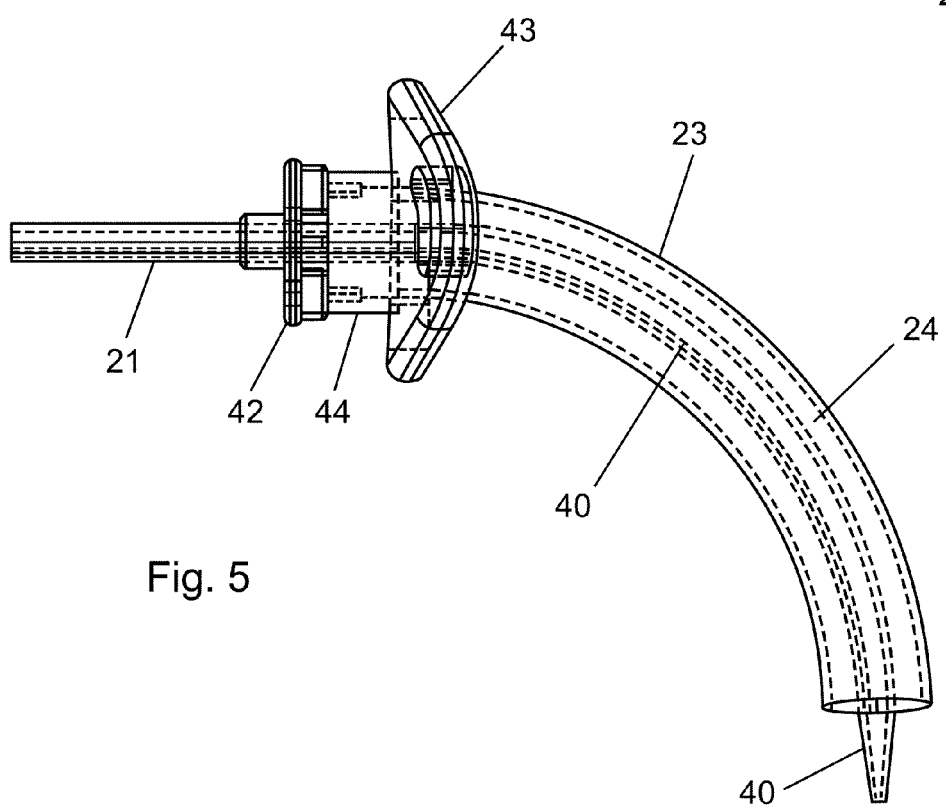
FIG. 5 shows a gas delivery circuit with a ventilation catheter placed into a trach tube patient interface with an open connection, with the ventilation catheter extending to that the distal tip protrudes out of the tip of the trach tube.

FIG. 5 describes a side view of a tracheostomy tube configuration where the ventilation catheter 40 extends past a tip of the trach tube 23. The gas exiting from the ventilation catheter 40 may entrain upper airway flow from the trachea T as well as some gas from inside the trach tube airflow channel 24 and from proximally outside the trach tube 23. If the connection between the ventilation catheter 40 and the trach tube 23 at the proximal end of the trach tube 23 is closed, there is no additional entrainment of air from ambient through the trach tube airflow channel 24, and the patient cannot breathe through that route. If, however, the trach tube 23/ventilation catheter 40 connection is open, the may be additional entrainment of air from ambient, depending on the exact location of the tip of the catheter, and the patient can breathe through that route as well as the upper airway route.

Figure 6:
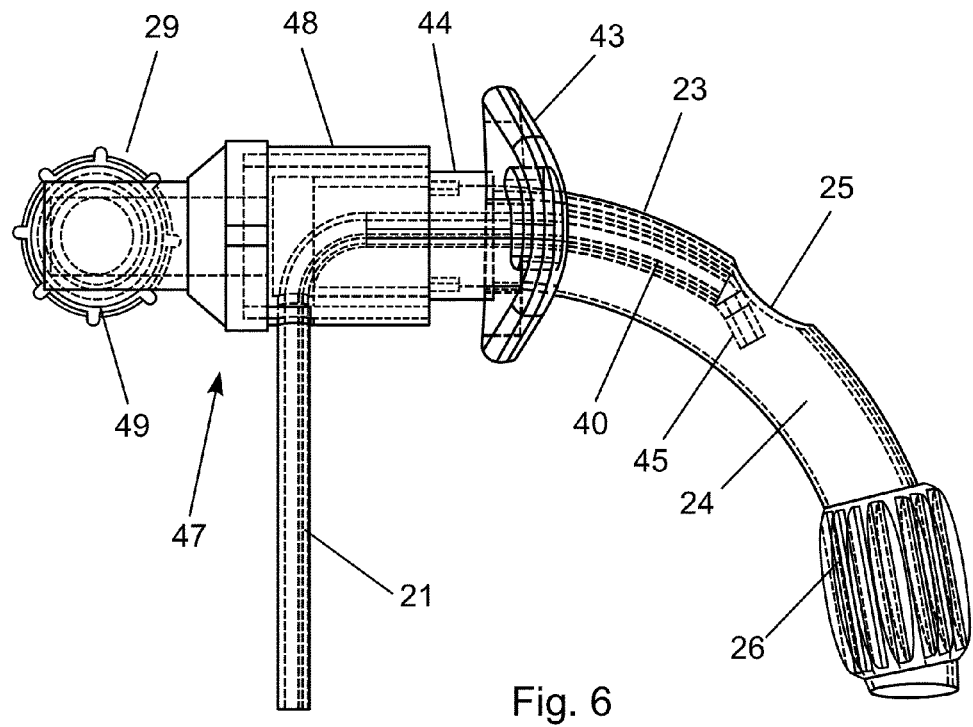
FIG. 6 shows a gas delivery circuit and ventilation catheter connected to a fenestrated cuffed trach tube patient interface with a swivel elbow connection, with the ventilation catheter distal tip positioned near the fenestration, and with the swivel elbow connector capped.

FIG. 6 describes a side view of a configuration in which the trach tube 23 includes one or more fenestrations 25 along its length. The ventilation catheter distal tip 45 nozzle may be located near the fenestration 25 to entrain air through the fenestration 25. In this case, the vacuum or entrainment chamber of the system may be both (a) the tracheal airway compartment above the fenestration 25 and (b) the trach tube 23 and swivel elbow connector 47 and ambient air outside the trach tube 23. A tracheostomy tube cuff 26 may prevent passage of air from the upper airway past the trach ventilation catheter 40. By adjusting the exact detailed dimensions of the configuration, such as fenestration dimensions and location, catheter tip dimensions and location, trach tube nozzle section dimensions, etc., the amount of entrained air can be increased or decreased for both the tracheal entrained air and the ambient entrained air. Entrainment from the trachea may be preferred in that the entrained air would include naturally humidified air. Sometimes entrained air through the trach tube from ambient can be preferred, for example, in the case of upper airway obstruction or in cases where the patient's upper airway is becoming dry in which case additional entrainment may not be desired. The ventilation gas delivery circuit 21 and ventilation catheter 40 may be attached to the trach tube connector 44 with a swivel elbow connector 47, which may have a female 15 mm distal connector 48 and a male 15 mm proximal connector 49. Optionally the proximal connector of the trach tube or swivel elbow connector can include the attachment of other features as will be described later. A connector cap 29 may seal the swivel elbow connector 47. In the case shown, the distal end of the connector 47 is capped with a cap 49, in which case the jet entrainment occurs through the trach tube fenestration 25 and the patient's spontaneous breathing occurs through the upper airway through the fenestration 25 when the cuff 26 is inflated, and if the cuff 26 is deflated spontaneous breathing occurs through both the fenestration 25 and also around the outside of the trach tube 23.

Figure 7:
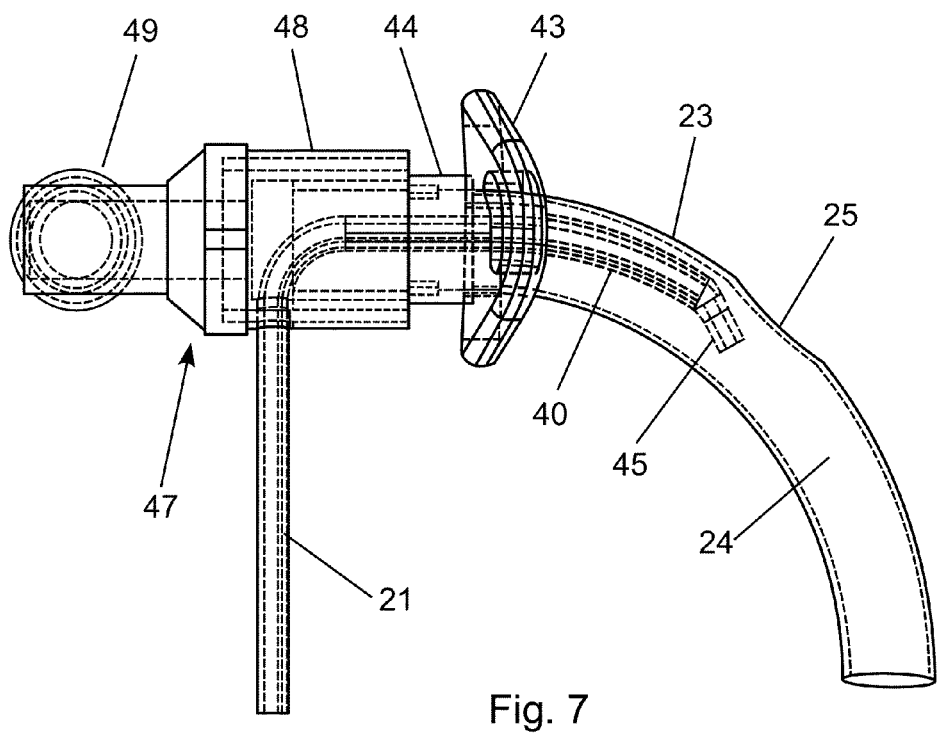
FIG. 7 shows a gas delivery circuit and ventilation catheter connected to a fenestrated trach tube patient interface with a swivel elbow connection, with the ventilation catheter distal tip positioned near the fenestration.

FIG. 7 describes a side view of a patient interface configuration in which the trach tube 23 is a fenestrated trach tube. In the case shown, the distal end of the connector 47 is not capped with a cap 49. In this case, the patient may spontaneously breathe through the open connector 47.

Figure 8:
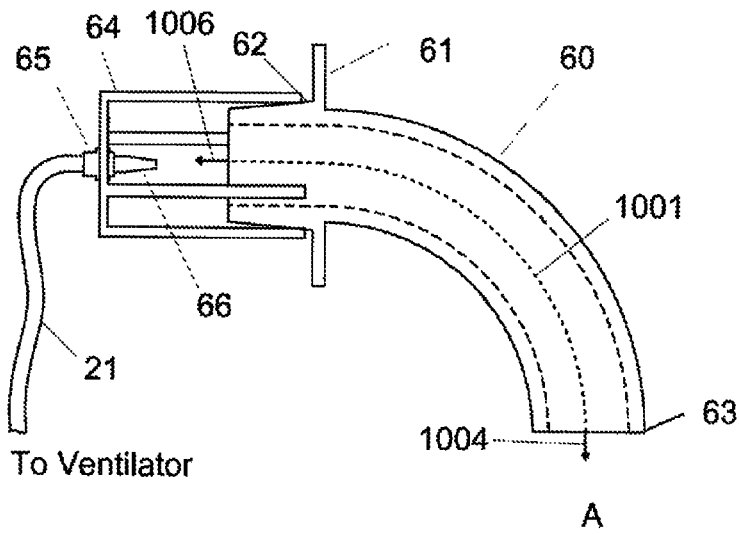
FIG. 8 shows a gas delivery circuit connected to an airway tube with a baffled connection, with the nozzle tip located a distance outside of the proximal end of the airway tube.

FIG. 8 describes a side view of an open interface. A gas delivery circuit 21 is attached to an airway tube 60 with a baffle attachment. The airway tube 60 has a hollow cylindrical configuration defined by a central lengthwise axis 1001 and may be an endrotracheal tube, a tracheostomy tube, a laryngectomy tube, or any other airway tube. The airway tube may include an airway tube flange 61. The airway tube 60 may also include an airway tube distal end 63 that is open and defined by an opening axis 1004, which may include a cuff. The tip of the gas delivery circuit may be configured as a gas delivery nozzle 66 and a tip of the gas delivery nozzle 66 may be positioned proximal to or a distance outside of the entrance to the airway tube 60. This end is also open and defined by an opening axis 1006. A baffle connector 64 may be open so that ambient air can be entrained, by the ventilator gas exiting the gas delivery nozzle 66. In FIG. 8, the baffle connector 64 is shown attached to an outside of the airway tube proximal connector 62: however, the baffle connector 64 may be attached to an inside surface of the airway tube 60, or connected to as proximal edge of the airway tube 60. Ideal distance between the gas delivery nozzle 66 and airway tube entrance varies depending on conditions such as type and size of the airway tithe 60, desired therapeutic effect, and ventilator drive pressures, as well as catheter and nozzle dimensions, however, exemplary spacing ranges from 2" to −2', and ideally 1.5" proximal to 0.5" recessed. The gas delivery nozzle 66 is attached to the baffle connector 64 with a baffle swivel connector 65 so the gas delivery circuit 21 can swivel to route the tubing where most convenient. The gas delivered by the gas delivery circuit 21 can be oxygen, air, air-oxygen mixtures, therapeutic, gases, or drugs as well. Optionally, therapeutic gases can be bled into the system. Additional details about the gas delivery system are described in FIGS. 28 and 38-40.

Embodiments of the present invention may impact efficacy. The location of the tip of the ventilation catheter relative to the tracheostomy tube, or more generically an airway tube, is a key primary contributor to the amount of air entrained, and, therefore, the physical efficiency of the system, and to the amount of volume and pressure that the ventilation system can create in the patient's lung. Increasing pressure or volume in the patient's lung is necessary for the system to be clinically efficacious. For example, an increase of inspiratory lung pressure from an unassisted value of −5 cmH$_2$O to an assisted value of −1 cmH$_2$O may reduce the inspiratory muscle work and provide relief and support to the patient. Or, an increase of lung pressure from an unassisted value of −5 cmH$_2$O to an assisted value of +5 cmH$_2$O may provide relief and even more support to the patient. In a spontaneously breathing patient, these pressure increases can be considered potential increases, as the patient effort may compensate by expending more or less breathing effort based on the sensation of the ventilation support. In a ventilator dependent patient or controlled breath, the pressure increases may apply. The higher the increase in lung pressure caused by the ventilator system, the higher the potential increase in lung volume, which is also efficacious in improving gas exchange. Also, for obstructive lung disease patients, the added support from the ventilation system may shorten inspiratory time, which may provide a longer time for exhalation and reduce dynamic hyperinflation. The work of breathing assistance provided by the potential of increased lung pressure may unload and rest the respiratory muscles, so that they have more strength and reserve which may help re-model the lung mechanics and potentially reduce static hyperinflation. In restrictive lung disease patients the potential for increased lung pressures and lung volumes may help compensate for the restrictive airways and stiff lung, giving the sensation that it is easier to breathe. For neuromuscular patients, the increased lung pressures and volume help compensate for the body's inability to neurologically or mechanically breathe adequately. Other contributors to the physically efficiency and clinical efficacy of the ventilation system include the exit velocity of gas exiting the ventilation catheter, the alignment of the velocity of the gas relative to the tip of the airway tube or the airway lumen, the gas volume surrounding and in the immediate vicinity of the ventilation catheter nozzle.

ambient air from outside the airway, and (2) airway air through the fenestration. This case can improve the efficiency of Case B, however, is still not as efficient as Case C. Another advantage of Case C is that it is less prone to performance degradation based on misalignment between the catheter tip and the airway tube tip.

Note, however, that Case A and Case B are advantageous over Case C in terms of delivering humidified gas to the lung. Case C delivers the most un-humidified gas because of the high amount of ambient air entrained verses Case A, which delivers the most humidified gas because the entrained gas is from the upper airway which is humidified by the nasal passage. Case B and Case C, however, can be modified by introducing artificial humidification with the ventilation and entrained gas, or by using a heat moisture exchanger. Some exemplary values of Case A, B and C are listed below in Table 1.

TABLE 1

| Case | Ventilator gas flow rate | Total entrained air (% of ventilator gas delivery) | Entrained air from ambient outside of airway tube (% of ventilator gas delivery) | Entrained air from airway above airway tube (% of ventilator gas delivery) | Pressure potential increase |
|---|---|---|---|---|---|
| A | 15 lpm | 93% | 56% | 37% | 0.6 cmH2O |
| B with Fenestrated Airway tube | 15 lpm | 167% | 150% | 17% | 1.4 cmH2O |
| B with non-fenestrated Airway tube | 15 lpm | 233% | 95% | 138% | 1.3 cmH2O |
| C | 15 lpm | 300% | 290% | 10% | 1.5 cmH2O |

Three cases may be considered for the location of the tip of the ventilation catheter with respect to the airway tube. In Case A (FIG. 5), the catheter tip may extend to, or past a distal tip of the airway tube. In Case B (FIGS. 4, 6 and 7), the catheter tip may be positioned approximately half way between the proximal and distal end of the airway tube. In Case C (FIG. 8), the catheter tip may be positioned outside of the proximal end of the airway tube.

In Case A, the jet has the opportunity to entrain gas in the airway. In the case that the airway is the trachea or another large airway, this volume of gas in the airway column is substantial. One skilled in the art of jet pump design might expect therefore that the Case A tip position would be the optimal configuration to optimize entrainment, compared to Case B and Case C. However, empirical examination reveals that Case B and Case C result in superior entrainment efficiency over Case A. In Case B, the jet entrains some air from outside the proximal end of the airway tube and this entrainment can exceed the entrainment of Case A. Case C provides the best entrainment efficiency, which may not be intuitive. One skilled in the art may think that the gas exiting the catheter tip outside of the airway tube would create turbulence at the entrance to the airway tube, and significantly degrade performance. However, empirical evaluation reveals that this is not the case and rather, the velocity flow profile is well organized as it enters the entrance to the airway tube, along with the entrained ambient air. Referring back to Case B, where the airway tube has an aperture near the position of the catheter tip, for example, the fenestration in a trach tube, the system has two potential sources of entrainment: (1)

The values above are based on a ventilator gas delivery of 15 lpm, which is near the low end of the range of ventilator flow rate in this invention. Typically the ventilator flow rate in this invention may be 15-40 lpm average flow rate, and 20-60 lpm peak flow rate. As the flow rate increases, the entrainment percentage increases in a linear relationship, and the pressure potential increase, increases in a squared relationship. Non-intuitively, the amount of air entrained from the upper airway in Case A is less than the ambient air entrained through the proximal end of the airway tube. Referring back to Case B, it may be beneficial if the axial centerline of the distal tip of the catheter is aligned with the axial centerline of the distal tip of the airway tube, so that the jet exiting the tip of the catheter does not collide with the inner wall of the airway tube. This alignment may preferably be within approximately 10 degrees of perfectly aligned. Entrainment performance may degrade due to turbulence and disorganized air flow velocity profiles occurring between the catheter tip and the airway tube tip.

Figure 9:
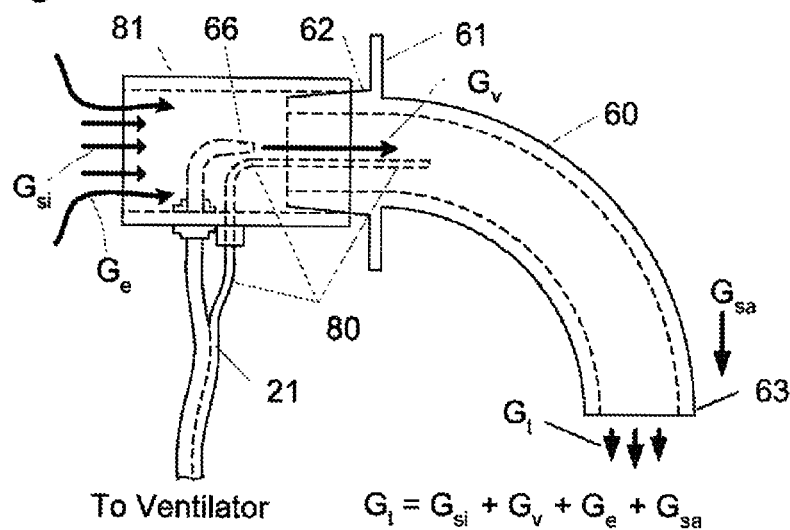
FIG. 9 shows a gas delivery circuit connected to an airway tube with an open adaptor, and shows the sources of gas being delivered to the airway, and shows a breath sensing extension tube.

FIG. 9 describes a side view of an open interface depicting sources of gas flowing into an airway A. Ventilator gas $G_v$ exiting the nozzle may entrain air $G_e$ from outside the airway tube 60. The patient may spontaneously draw in ambient air from outside the airway tube $G_{si}$, and from the upper airway $G_{sa}$. The total gas delivered into the lung $G_t$, is a combination of these four sources. The gas delivery circuit 21 in FIG. 9 is also shown with a breath sensing line 80. The purpose of the breath sensing line 80 is to measure the breathing pressure of the patient, to synchronize the ventilator functions to the patient's breathing and to track the respiratory parameters of the patient. At or near a distal end of the gas delivery circuit 21, the breath sensing line may divide from the catheter and extend deeper into the airway tube 60 than the gas delivery nozzle 66. The deeper extension may allow for more sensitive detection of airway breathing pressures. The extension can extend to the airway tube distal end 63 or beyond the airway tube distal end 63. The breath sensing line 80 can also attach to a lumen in the wall of the airway tube 60 or be integral to the construction of the airway tube 60 to sense the airway pressure. An airway tube adapter 81 may couple the gas delivery circuit 21 and/or breath sensing line 80 to the airway tube 60.

Figure 10:
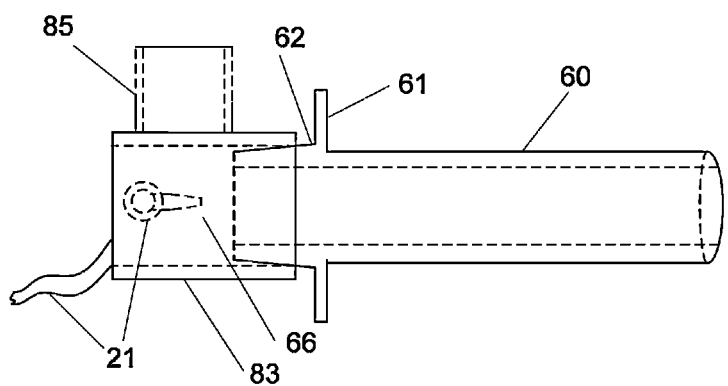
FIG. 10 shows a gas delivery circuit connected to an airway tube with an open elbow connector.
Figure 11:
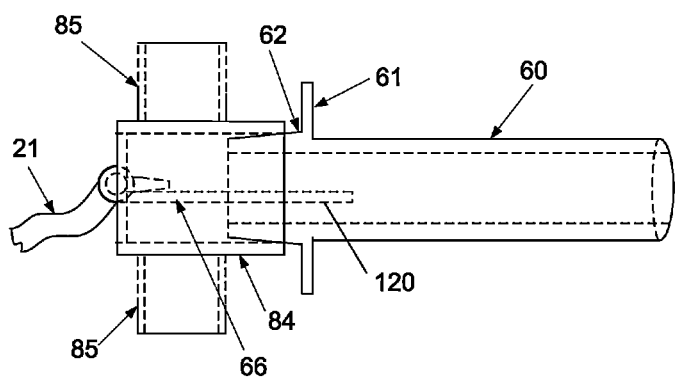
FIG. 11 shows a gas delivery circuit connected to an airway tube with an open T connector.
Figure 12:
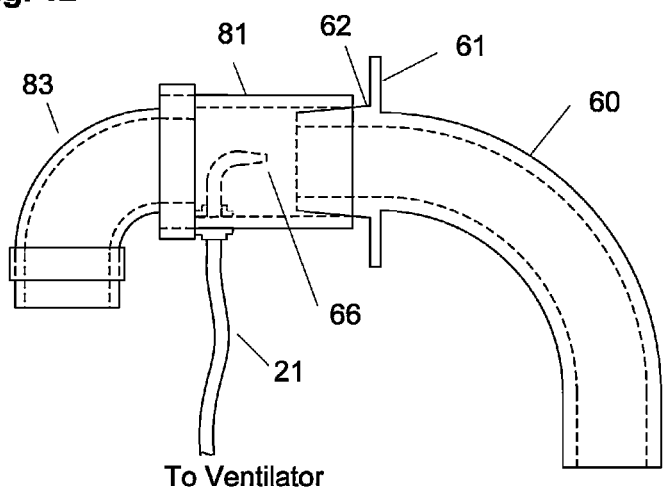
FIG. 12 shows a gas delivery circuit connected to an airway tube with an open swivel elbow connection.

FIG. 10 describes a partial cross-sectional top view of an open interface with an airway tube side connector 82. The airway tube side connector 82 may be attached to a proximal end of the airway tube 60. The proximal end of the airway tube side connector 82, opposite to the airway tube 60, may be open to ambient air so that the gas exiting the gas delivery nozzle 66 entrains ambient air through the airway tube side connector 82. In FIG. 10, the path from ambient air into the airway tube side connector 82 and into the airway tube 60 is a relatively straight path with no or minimal abrupt directional changes of the air required. A side connection 85 of the airway tube side connector 82 may be available for attachment of a respiratory accessory, such as oxygen attachment, etc. Alternatively to the design shown, the proximal side can either be open as shown or closed. Any reasonable configuration of connectors can be used, such as Y-shaped, T-shaped or L-shaped connectors can be used. For example, FIG. 11 describes an open interface with an airway tube T adapter 84, with two open side connections 85 to allow passage of air and for connection of any necessary accessories. The proximal end of the airway tube T adapter 84 opposite the airway tube 60 is shown closed in this example, although it can be open or closed. Also, for example, FIG. 12 describes an open interface with an airway tube elbow connector 83, which preferably swivels. If an accessory is attached to the airway tube elbow connector 83 the swivel may help position it as desired.

Figure 13:
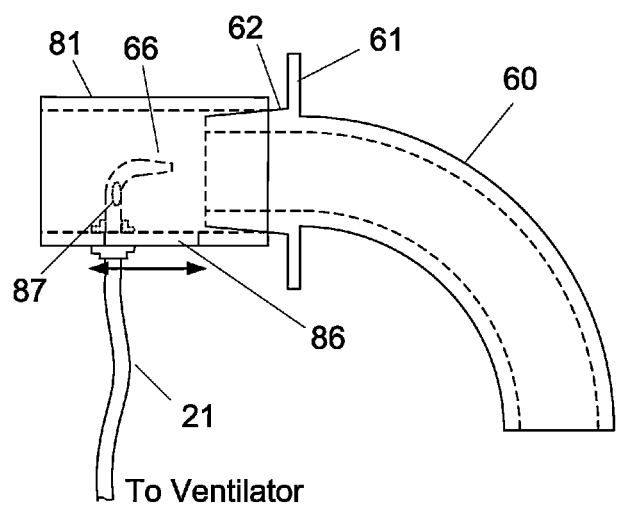
FIG. 13 shows a gas delivery circuit connected to an airway tube with an open adaptor connector with a sliding nozzle adjustment.

FIG. 13 describes an open interface with an adjustable gas delivery nozzle 66. The gas delivery nozzle 66 may move proximally and distally with respect to the airway tube 60 in a guide or nozzle adjustment slot 86 in the airway tube adapter 81. The purpose of being able to adjust the position is to increase or decrease the amount of entrainment, and the resultant airway pressure created, based on the needs of the patient. A signal from a pressure sensing port 87 can be used to determine the appropriate location of the gas delivery nozzle 66. For example, if it is desired to maximize entrainment, the gas delivery circuit 21 can be moved until the signal from the pressure sensing port 87 registers a peak amplitude. A ventilator user interface can indicate this position status to the user. Or, for example, if it is desired to achieve a certain amount of entrainment, the gas delivery circuit 21 position can be moved until the proximal pressure sensing port 87 registers the desired characteristic signal expected for that amount of entrainment.

Figure 14:
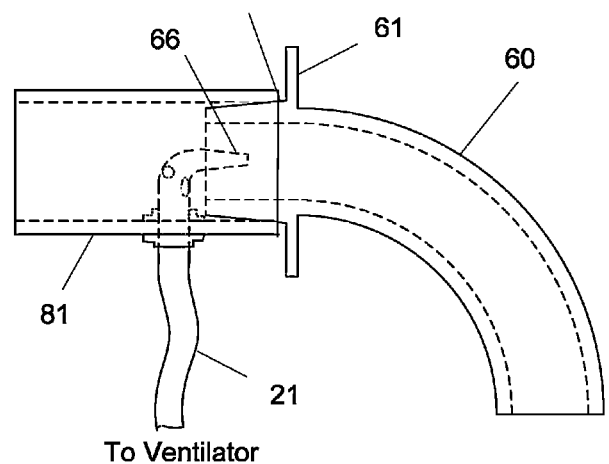
FIG. 14 shows a gas delivery circuit connected to an airway tube with an open adaptor connection, with the gas delivery nozzle located slightly inside the airway tube proximal end.

FIG. 14 describes an open interface with the nozzle of the gas delivery circuit positioned slightly inside a proximal end of the airway tube 60, rather than positioned at a distance outside of the airway tube 60. The gas delivery nozzle 66 may be located in a section of the airway tube that possesses a straight axial cross section, such that rotation of the connection between the gas delivery circuit 21 and the airway tube 60 does not change the alignment of the gas delivery nozzle 66 relative to the airway tube axial centerline. By contrast, if the nozzle tip were positioned at a depth within the airway tube where the airway tube axial centerline is arcuate or angled, rotation of the connection between the gas delivery circuit 21 and the airway tube 60 would cause misalignment of the jet with the airway tube 60 and poor aerodynamics, which would be unfavorable to the therapeutic results. Therefore, this arrangement may allow the user to attach the two pieces without being concerned about rotational alignment, and/or the attachment can include a rotational swivel to allow the gas delivery circuit tubing to be routed away from the patient as desired.

Figure 15:
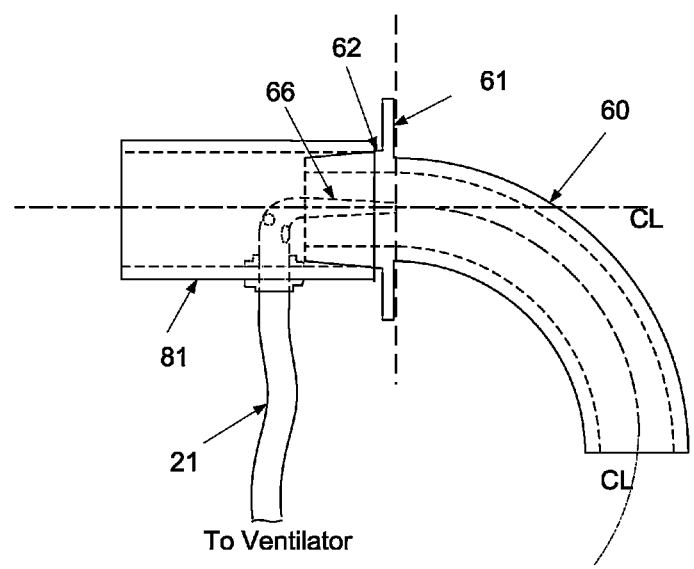
FIG. 15 shows a gas delivery circuit connected to an airway tube with an open adaptor connector, with the gas delivery nozzle located a distance inside of the airway tube.

FIG. 15 describes an open interface with the distal tip of the gas delivery nozzle 66 positioned near the transition of the straight section of the airway tube 60 at its proximal end, to the curved section of the airway tube 60.

Figure 16:
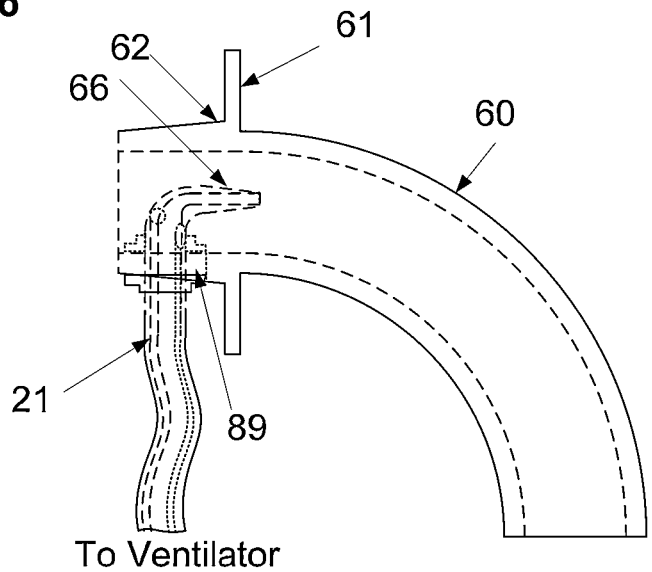
FIG. 16 shows a gas delivery circuit with a low profile connection connected directly to the proximal end of an airway tube.
Figure 17:
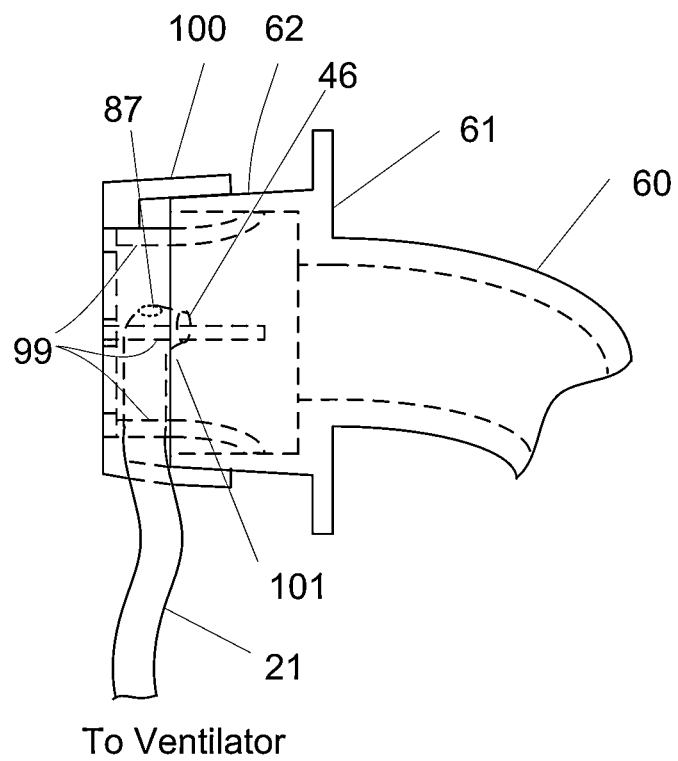
FIG. 17 shows a gas delivery circuit connected to an airway tube with a low profile open connection with the connection inside the proximal end of the airway tube.

Previous examples of the open airway interface describe connections to the patient interface that protrude away from the patient. FIGS. 16 and 17 describe an alternative connection that is low profile.

FIG. 16 describes an open interface with the catheter attached to a nozzle connection slot 89 in the proximal end of the airway tube 60. The nozzle connection slot 89 may avoid the need for a bulky connector. The gas delivery circuit 21 can attach directly to the nozzle connection slot 89 with a removably attachable and secure connection. A slotted proximal end of the airway tube 60 can be the tube itself, a 15 mm connector, or an outer cannula or an inner cannula of the airway tube.

FIG. 17 describes an open interface with a low profile gas delivery nozzle 101 and low profile connector 100 coupled to the airway tube 60, with clips 99 engaging the outside and/or inside of a proximal end of the airway tube 60. These low profile connections may be advantageous when the patient is spontaneously breathing and using the therapy when in public, such that the gas delivery circuit 21 and interface can be more concealed. The clips 99 of the low profile connection may occupy as little of the inner diameter of the airway tube 60 as possible so as to not restrict flow through the airway tube 60. The clips 99 can be radially expanding so that the clips 99 engage with adequate force against the inside wall of the airway tube 60 near the proximal end, for example with 2-10 lbs radial force, preferably 4-6 lbs. The clips 99 may hold with a friction fit. The clips 99 can be plastic or metal, for example, ULTEM or nylon, or stainless steel or NITANOL, respectively. The low profile connection can also include one or more external clips that attach to an outside of the proximal end of the airway tube, to pinch the wall of the airway tube to attach to the airway tube 60 with adequate force. To facilitate the low profile design, the gas delivery circuit 21 can include a low profile gas delivery nozzle 101, which may include a ventilation gas delivery port 46 formed into a side wall of the gas delivery nozzle 101 at a tip of the gas delivery circuit 21. The gas flow path may be curved rather than at a right angle flow path near the tip to allow the flow profile of the gas to develop appropriately before exiting the gas delivery nozzle 101.

Figure 18:
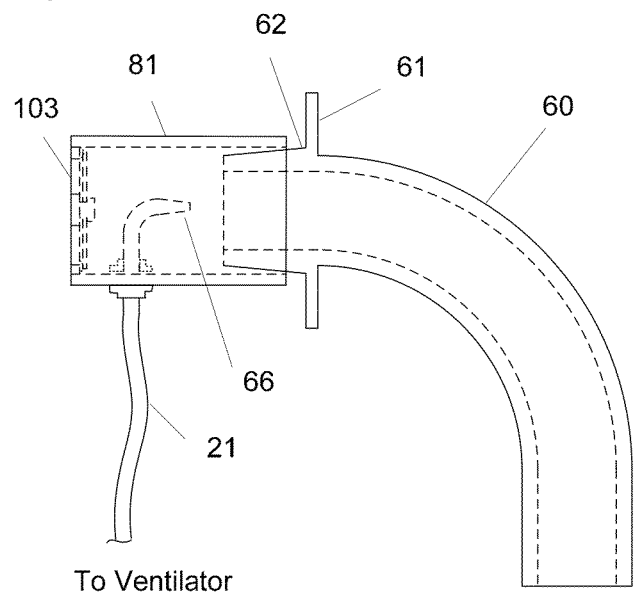
FIG. 18 shows a gas delivery circuit connected to an airway tube with an open adaptor connection, with an inspiratory valve on the proximal end of the inspiratory valve.
Figure 19:
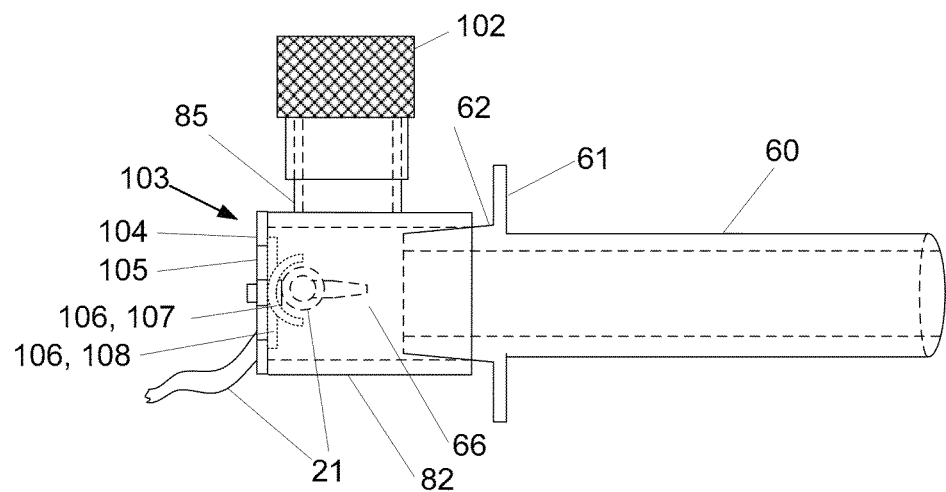
FIG. 19 shows a gas delivery circuit connected to an airway tube with an open elbow adaptor with a side connector, with a HME attached to the side connector and with an inspiratory valve.

FIGS. 18 and 19 show an open interface in which the gas delivery circuit 21 is attached to an airway tube 60 with an open airway tube adaptor 81 or airway tube connector with side attachment 82. The airway tube adaptor 81 or airway tube side attachment may include an inspiratory valve 103. FIG. 18 shows the inspiratory valve 103 as part of a straight airway tube adaptor 81 and FIG. 19 describes an airway tube connector with side attachment 82 coupled to an airway tube 60. The airway tube connector with side attachment 82 may include an inspiratory valve 103 at an end of the airway tube connector with side attachment 82 opposite the airway tube 60, and a respiratory accessory attached to the side connector of the airway tube connector with side attachment 82. In the example shown, the accessory is a heat and moisture exchanger (HME) 102, which traps exhaled moisture which can be returned to the patient during inspiration. The inspiratory valve 103 is typically a low resistance, low cracking pressure inspiratory valve, which easily opens to allow entrainment of ambient air with the jet exiting the nozzle. For reference, the inspiratory valve 103 is shown both in the closed state 108 and in the open state 107. The inspiratory valve 103 may include a valve seat 104, a valve port 105, and/or a valve diaphragm 106. Inspired air may be drawn through the inspiratory valve 103, and optionally also through the HME 102. The air entrained by the jet exiting the gas delivery nozzle 66 may help draw humidified air trapped by the HME 102 back into the patient's airway during inspiration. A purpose of the inspiratory valve 103 may be that during exhalation some exhaled air is forced to vent through the upper airway past the larynx, thus enabling phonation. Components other than an HME 102 can be used as will be described later. In the various embodiments described with an inspiratory valve 103, the inspiratory valve 103 may include flow ports that permit venting of exhaled gas such that enough gas can be exhaled while maintaining a back pressure to simulate pursed lips breathing. Cracking pressure of the inspiratory valve 103 may be typically less than 2 cwp, and preferably 0.3-0.8 cwp. Airflow resistance of the inspiratory valve 103 may be typically less than 10 cwp/L/sec, and preferably less than 5 cwp/L/sec.

FIG. 20 describes an open interface with a gas delivery circuit 21 and an airway tube connector with side connection 82 coupled to an airway tube 60. In FIG. 20, an exhalation PEEP valve 109 is attached to the side connection of the airway tube connector with side connection 82 and the side opposite the airway tube 60 includes an inspiratory valve 103. Therefore, the configuration is open to ambient air during inspiration and partially closed to ambient air during exhalation. During exhalation the exhalation PEEP valve 109 allows some exhaled airflow, but with a back pressure to create a desired PEEP level, for example 5 cwp. The resistance of the exhalation PEEP valve 109 may be for example 5-20 cwp/L/sec to create the desired PEEP level. The PEEP level can be adjusted to create the PEEP level desired. In FIG. 20, the exhalation PEEP valve 109 is a ball and cage valve with a spring. The tension on the spring determines the air flow resistance of the exhalation PEEP valve 109. In addition to an exhalation PEEP valve 109, the valve can be an expiratory valve or pressure relief valve, or any combination of the above.

FIGS. 21 and 22 show an open airway system with a gas delivery circuit 21 attached to an airway tube 60 with an airway tube adapter 81, and with an airway sensing extension line 120 extending into the airway tube 60 and/or airway of the patient. In FIG. 21 the airway sensing extension line 120 extends from the airway tube adaptor 81 into a channel of the airway tube 60. The airway sensing extension line 120 can extend partway into the airway tube's length as shown, or can extend to a distal tip of the airway tube 60 or beyond the distal tip of the airway tube 60. The airway sensing extension line 120 may include a distal sensing port 121 at or near the distal tip of the airway sensing extension line 120, and may include a proximal sensing port 122 near the proximal end of the airway sensing extension line 120. The proximal sensing port 122 and distal sensing port 121, when used together can determine air flow through the channel of the airway tube 60 by applying the Hagen-Poiseuille equation. Because the jet typically creates a negative pressure in the zone around the gas delivery nozzle 66, a true pressure measurement may not be possible; however, a microprocessor in the ventilator can apply a correction factor to the measured value to obtain a derived pressure measurement. Using the two pressure sensing ports to determine airflow through the airway tube 60 allows for the system to determine the amount of entrainment and amount of spontaneously inspired air flow through the airway tube. This information can be used to determine total volume delivered and can be used to adjust the ventilator settings to create the desired therapeutic levels.

FIG. 22 describes an alternative configuration to FIG. 21 where an airway tube sensing line 123 is integrated into the airway tube 60. The gas delivery circuit 21 may include a sensing line connector 126 that connects to the airway tube sensing line 123 in the airway tube 60. The airway tube sensing line 123 may extend to the tip of the airway tube 60, or alternatively can terminate in an airway tube distal sensing port 124 positioned somewhere along the length of the airway tube 60, or alternatively the airway tube sensing line 123 can include multiple sensing ports, including an airway tube proximal sensing port 125 and/or the airway tube distal sensing port 124. Alternatively the airway tube 60 or gas delivery circuit 21 can include multiple sensing line extensions.

Figure 23:
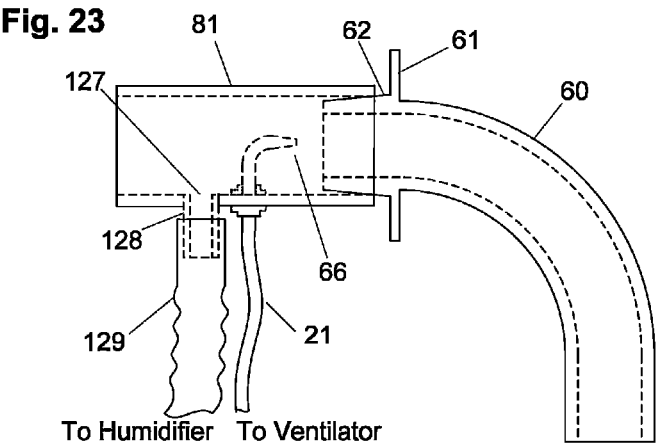
FIG. 23 shows a gas delivery circuit connected to an airway tube with an open adaptor with a humidification delivery attachment.

FIG. 23 describes an open interface with a humidification connector 128 for a humidification delivery hose 129. In this embodiment, heated humidified air may be delivered to the airway tube adapter 81 via a humidification delivery port 127 so that when the patient inspires, or when the Jet exiting the nozzle entrains ambient air, the air being drawn into the interface and patient's airways and lungs is humidified. The artificially humidified air may compensate for the dry air or oxygen being administered by the gas delivery catheter 21, and may also compensate for the drying of the airways that might occur by convective airflow of the ventilation gas along the airway mucosa. The humidity can be generated at the ventilator by a traditional heated humidifier, or can be generated by a vaporizer or aerosolizer or misting system. A temperature sensor (not shown) near the open interface can be provided to send a temperature signal back to the humidifier to adjust or limit the vapor output and maintained the delivered vapor at a safe temperature. The humidified gas can be air, oxygen or blended mixtures.

Figure 24:
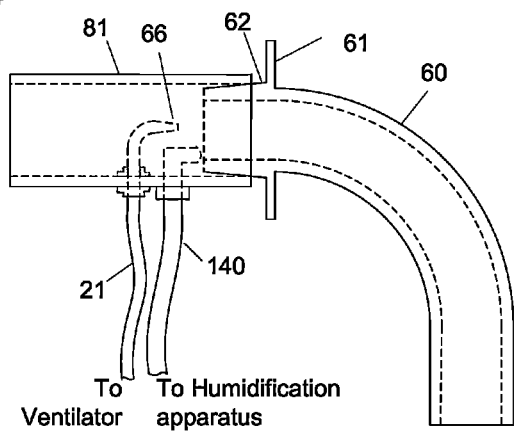
FIG. 24 shows a gas delivery circuit connected to an airway tube with an open adaptor with a humidification catheter attached.

FIG. 24 describes an open interface with a vapor or mist humidification catheter 140. In this embodiment, the humidification catheter 140 may be attached to the airway tube adapter 81 in addition to the gas delivery circuit 21. The humidification catheter 140 may deliver moisture to the airway in the form of vapor, mist, or water droplets. The moisture can be fed under pressure to exit the distal end of the catheter, or can be entrained out of the distal end of the catheter by the ventilation catheter Jet, or both. The mist catheter can be a portion of the ventilation catheter tubing, or can be separate.

Figure 25:
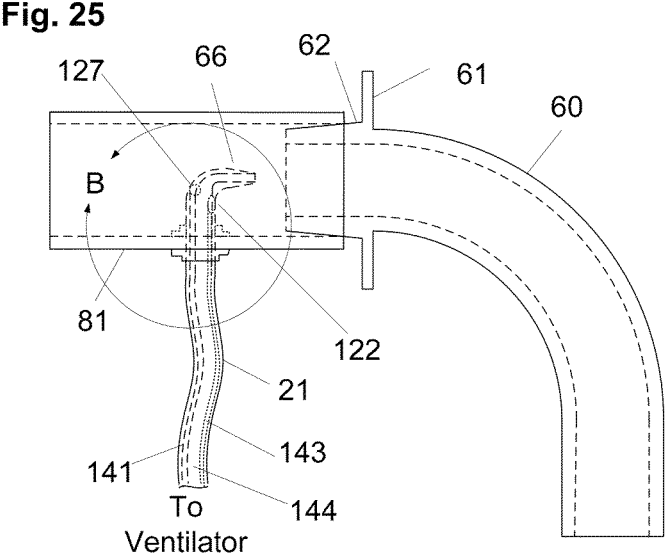
FIG. 25 shows a gas delivery circuit connected to an airway tube with an open adaptor with integral breath sensing and humidification delivery channels in the gas delivery circuit.
Figure 26:
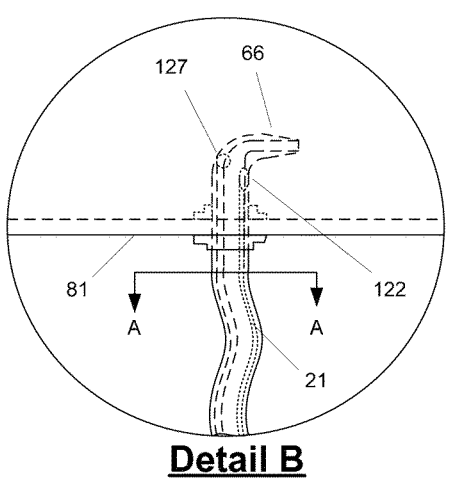
FIG. 26 shows a close up view of the nozzle of the configuration shown in FIG. 25.
Figure 27:
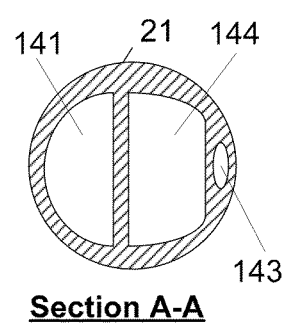
FIG. 27 shows a cross sectional side view of the gas delivery circuit shown in FIG. 25.

FIG. 25 describes an open interface with a humidification channel 141 and humidification delivery port 127 integral to the gas delivery circuit 21 and gas delivery nozzle 66, rather than a separate attachment for the mist catheter as shown in FIG. 24. FIG. 26 describes an enlarged view of the catheter tip at section B of the system in FIG. 25. FIG. 27 describes a cross section of the ventilation catheter at line A-A of FIG. 26. Moisture is conducted to the distal end of the gas delivery circuit 21 in a humidification channel 141. The source or generation of the moisture can be by heated humidification or aerosolization, and the moisture can be fed to the distal end of the catheter under pressure, or can be entrained out of the distal end by the ventilation catheter Jet, or both. Alternatively, moisture can be brought to the distal end of the catheter in the ventilation gas delivery channel 144, by entraining or mixing moist gas into the ventilation gas delivery channel 144 at some location between the ventilator and the patient. A breath sensing lumen 143 may also be included in the ventilation gas delivery circuit 21.

Figure 28:
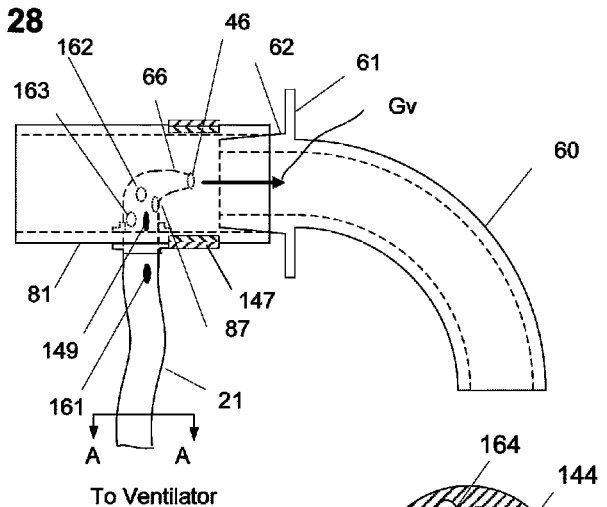
FIG. 28 shows a gas delivery circuit connected to an airway tube with one or more sensing ports.

FIG. 28 describes an embodiment of the invention in which the amount of oxygen delivered by the therapy is adjustable, and/or monitored, and/or controlled. The gas delivery circuit 21 may include an oxygen delivery port 162 or bleed port, an oxygen and/or carbon dioxide sensing port 163, and a pressure sensing port 87. In this embodiment, air rather than oxygen is delivered by the gas delivery nozzle 66 and oxygen is supplied via an oxygen delivery lumen 164 and oxygen bleed port. The oxygen may be delivered into the airway tube adapter 81 where it is entrained by the jet exiting the gas delivery nozzle 66. Optionally, the oxygen is drawn out of the oxygen delivery port 162 and oxygen delivery lumen 164 by being entrained by the ventilation gas jet. An oxygen and/or carbon dioxide sensing port 163 and oxygen and/or carbon dioxide sensing lumen 165 may be used to draw gas from the airway tube adapter 81 back to a sensor, typically at the ventilator, to determine the concentrations of oxygen in the gas in that area, both during exhalation and at other times of the respiratory cycle, to determine to the amount of oxygen in the patient's airway and lungs. The concentration detected can be used to increase or decrease the amount of oxygen being bled into the system, in order to achieve the desired fractional inspired oxygen (FIO2). In addition, the jet amplitude and duration can be varied in order to achieve the desired FIO2. Alternatively, the jet parameters and the oxygen bleed in parameters can be selected from a predetermine set of values in order to achieve the desired FIO2 level. In the example shown the oxygen can be bled in using a lumen in the gas delivery circuit, however, it can also be bled in from a separate catheter or tubing that is attached to the connector. FIG. 28 also describes an optional in line thermal sensor 149 and a reference thermal sensor 161, which can be used to measure respiration by temperature change. An adapter swivel 147 connection is also shown to help orient the airway tube adapter 81 to the airway tube 60 as desired.

Figure 29:
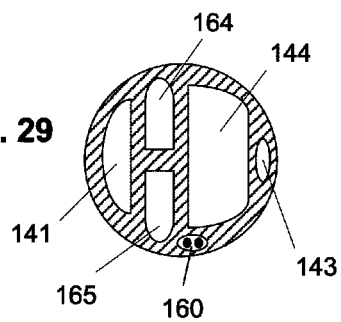
FIG. 29 shows a cross section along section A-A of FIG. 28.

FIG. 29 describes a cross sectional view of the system in FIG. 28 at line A-A, showing the ventilation gas delivery channel 144, the oxygen delivery lumen 164, oxygen and/or carbon dioxide sensing lumen 165, a humidification channel 141, a breath sensing lumen 143, and a thermal sensor wire 160 and related lumen.

Figure 30:
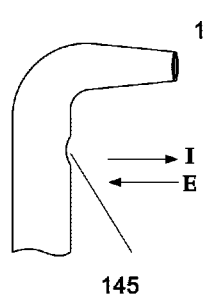
FIG. 30 shows a close up view of the nozzle of FIG. 28 with breath sensing ports facing the expiratory flow.
Figure 31:
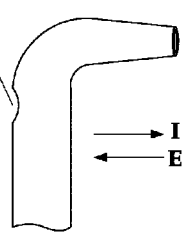
FIG. 31 shows a close up view of the nozzle of FIG. 28 with breath sensing ports facing the inspiratory flow.
Figure 32:
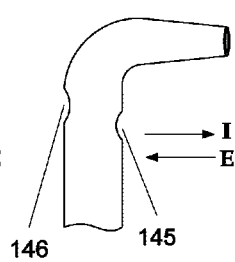
FIG. 32 shows a close up view of the nozzle of FIG. 28 with breath sensing ports facing the inspiratory and expiratory flow.

FIGS. 30-32 describe different locations and configurations of the airway pressure sensing port 87 at a distal tip of the gas delivery circuit 21. FIG. 30 shows the sensing port 145 positioned on the anterior side of the distal tip of the gas delivery circuit 21 and oriented orthogonal to the direction of exhaled airflow. This location may be extra sensitive during exhalation since exhaled gas may impinge on the port without any signal losses or artifacts. FIG. 31 describes the gas delivery circuit 21 with a pressure sensing port 146 facing the direction of inspired air flow. This location may be extra sensitive during inspiration since inspired gas may impinge on the port without any signal losses or artifacts. FIG. 32 describes the gas delivery circuit 21 with two pressure sensing ports, one facing the direction of inspired flow 146 and one facing the direction of exhaled flow 145. This configuration may provide improved sensitivity for both the inspiratory and expiratory phases. The sensing port can also be oriented to be parallel to breathing airflow and can be positioned on the lateral sides, the superior surface or the inferior surface of the nozzle.

Figure 33:
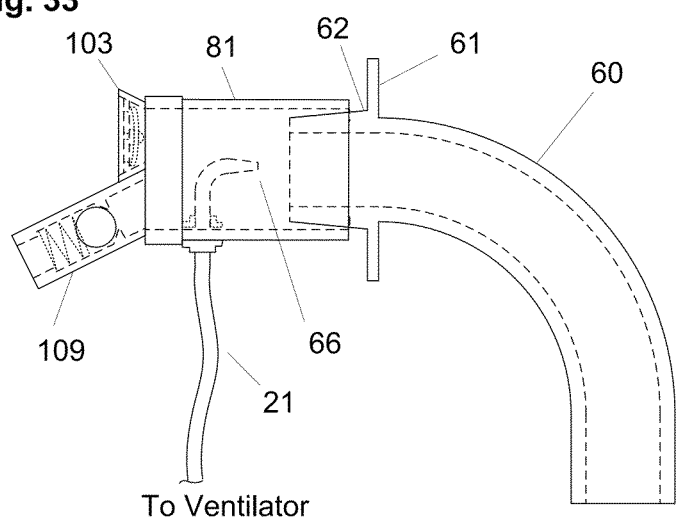
FIG. 33 shows a gas delivery circuit connected to an airway tube with an open adaptor, and with a valve attached to the open adaptor to convert to a closed or partially closed system.
Figure 34:
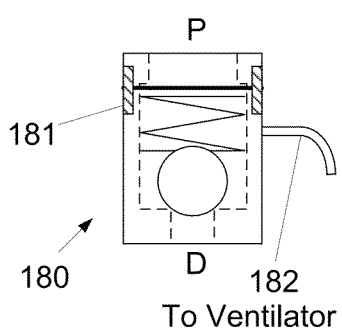
FIG. 34 shows a close up view of the valve shown in FIG. 33.
Figure 35:
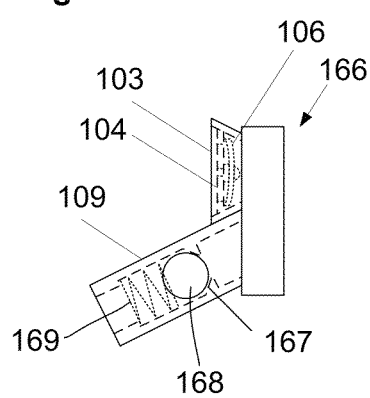
FIG. 35 shows an adjustable valve which is an alternate to the valve shown in FIG. 33.

FIGS. 33-35 describe an embodiment of the invention in which the open interface can be converted into a closed or partially closed interface. FIG. 33 describes an open interface that is converted to a partially closed interface by attaching a valve assembly to the airway tube adapter 81 of the open interface. The valve assembly may include an inspiratory valve 103 and an exhalation PEEP valve 109. The exhalation PEEP valve 109 may include a PEEP valve and a PEEP/PIP relief valve 180. The inspiratory valve 103 may be a low cracking pressure low resistance valve that allows for entrainment of ambient gas from the ambient side of the inspiratory valve 103 to the airway tube 60 and patient. FIG. 34 describes a detailed view of the valve assembly of the system described in FIG. 33. In the example shown, the exhalation valve 109 is a ball check valve, with an exhalation valve seat 167, an exhalation valve ball 168, an exhalation valve spring 169 to make it a normally closed valve, however, any type of check valve or one way valve can be used, such as a duck bill valve, a diaphragm valve or a leaflet valve. The exhalation valve 109 may include a valve adjustment 181 and/or a valve pilot pressure line 182. During spontaneous breathing, the valve is typically a passive valve and is opened with a light pressure, such as 1-10 cmH$_2$O, preferably 1-3 cmH$_2$O, which allows the gas volume in the patient's lung and airways to exhale. During controlled mechanical ventilation when the patient is not breathing on his or her own, the valve can be switched to an active valve which is cycled open by the ventilator controls when the inspiratory phase is completed. In this case the exhalation valve includes a pilot signal line that transmits a pressure signal from the ventilator to provide the opening or closing control to the valve. FIG. 35 is detailed view of an alternative inspiratory/expiratory valve 166 of the system described in FIG. 34, in which a pilot signal from the ventilator regulates the opening and closing of the exhalation valve 109 and/or the PEEP level that the exhalation valve 109 creates, and in which there is a PEEP adjustment to set the PEEP setting and pressure relief setting. Exhaled air may move from a distal end D to a proximal end P.

Figure 36:
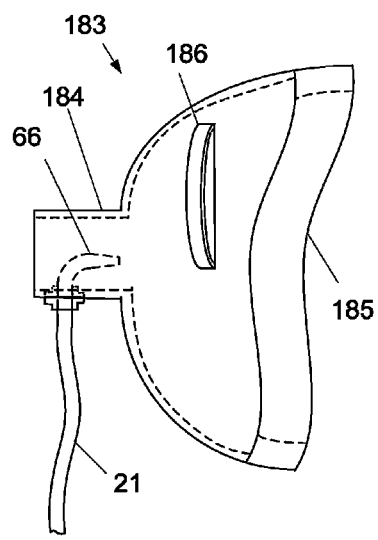
FIG. 36 shows a gas delivery circuit connected to a patient interface mask.

FIG. 36 describes an open airway ventilation system in which the gas delivery circuit 21 is connected to a mask-type patient interface, such as a ventilation mask 183. A mask proximal connector 184 may be open to allow ambient air flow in and out of the ventilation mask 183. The distal tip and gas delivery nozzle 66 of the gas delivery circuit 21 may be placed inside the ventilation mask 183 and/or inside the mask proximal connector 184. The system may then provide a positive pressure in the ventilation mask 183 by the jet and entrained ambient air. The patient may breathe spontaneously from the source of positive pressure in the ventilation mask 183 as well as ambient air through the ventilation mask 183. The ventilation mask 183 may include a ventilation mask seal 185 and/or one or more mask strap connections 186.

Figure 37:
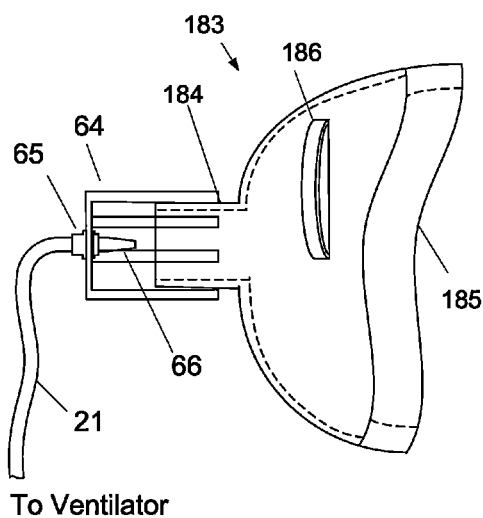
FIG. 37 shows a gas delivery circuit connected to a patient interface mask with a nozzle outside the patient interface mask.

FIG. 37 describes an open airway ventilation system in which the gas delivery circuit 21 is connected to a mask-type patient interface, such as a ventilation mask 183. A mask proximal connector 184 may be open to allow ambient air flow in and out of the ventilation mask 183. The distal tip and gas delivery nozzle 66 of the gas delivery circuit 21 may be placed outside the ventilation mask 183 and outside the mask proximal connector 184. The gas delivery circuit 21 may be coupled to the ventilation mask 183 and/or the mask proximal connector 184 via a baffle connector 64 and/or baffle swivel connector 65. The system may then provide a positive pressure in the ventilation mask 183 by the jet and entrained ambient air. The patient may breathe spontaneously from the source of positive pressure in the ventilation mask 183 as well as ambient air through the ventilation mask 183. The ventilation mask 183 may include a ventilation mask seal 185 and/or one or more mask strap connections 186.

Figure 38:
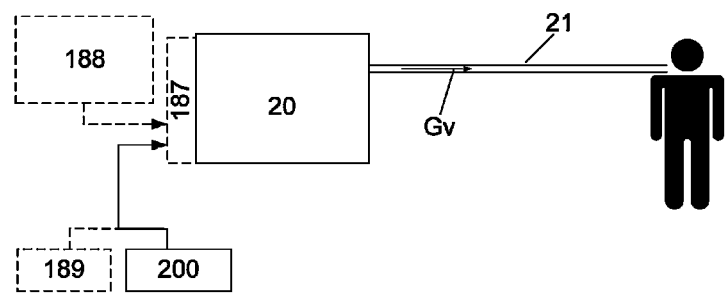
FIG. 38 shows a system schematic of the open airway ventilation system when used with an external gas supply.

FIG. 38 describes a system schematic of an embodiment of the overall invention, in which the ventilator 20 is powered by compressed oxygen and delivers a high oxygen concentration to the patient, which would be useful in COPD or ARDS applications in which the patient often requires enriched concentrations of oxygen to be delivered. The gas source can be a variety of sources; the ventilator 20 can be powered by a compressed oxygen supply 200, such as a cylinder or compressed oxygen wall supply, as in a hospital setting. In this case 100% oxygen is delivered to the patient from the ventilator 20, and the resultant FIO2 of the therapy is a result of the 100% oxygen plus the entrained ambient air. For example, if 120 ml of 100% oxygen is delivered, and there is 100% entrainment of ambient gas, i.e., 120 ml of air is entrained, plus there is an additional 120 ml of ambient air inspired spontaneously by the patient, then the total gas received by the lungs is 360 ml at 47.33% FIO2. Optionally, compressed air from a compressed air supply 189 can be connected to the ventilator 20 and blended by a blender 187 coupled to an external compressor 188. The compressed air may be blended with the compressed oxygen before entering the ventilator 20 or blended while inside the ventilator 20 to adjust the oxygen concentration of the ventilation gas being delivered.

Figure 39:
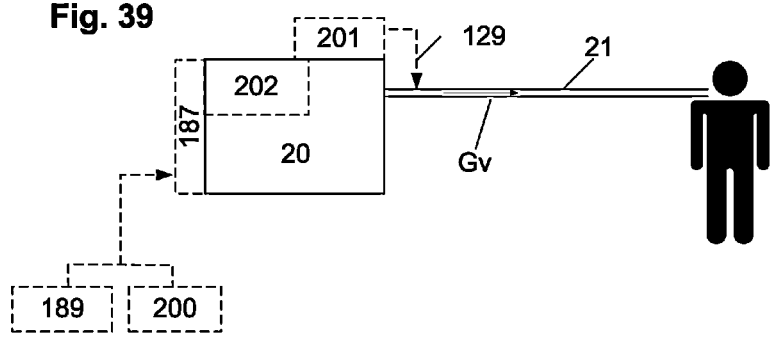
FIG. 39 shows a system schematic of the open airway ventilation system when used with an internal compressor, a blender an optional external gas supply and an optional humidification unit.

FIG. 39 describes a system schematic of an embodiment of the overall invention, in which the ventilator 20 is powered by blended compressed air and oxygen, and delivers a blended concentration of air/oxygen to the patient. In this embodiment, the ventilator 20 may include an internal compressor-turbine 202, which would be useful in a neuromuscular application, in which high oxygen concentrations is often not required by the patient. Optionally, the compressor-turbine may be external. Compressed air and oxygen may be blended using a blender 187 external or internal to the ventilator 20, to select and create the oxygen concentration required for the situation. FIG. 44 also shows humidity being bled into the system from a humidifier unit 201 via a humidification delivery hose 129, as previously described.

Figure 40:
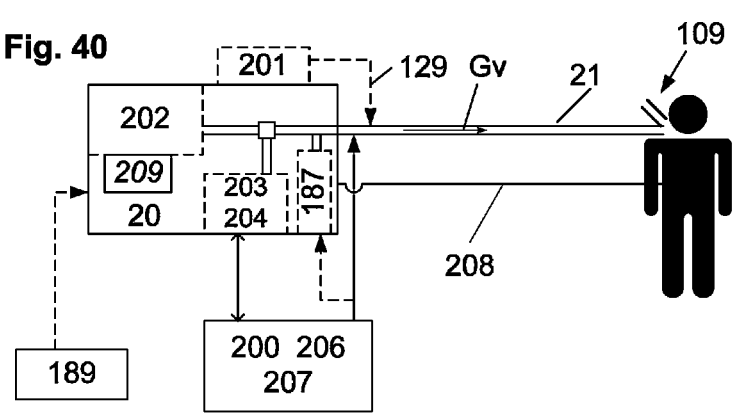
FIG. 40 shows a system schematic of the open airway ventilation system that is converted to a closed or partially closed system, with a gas composition analyzer, an internal blender, external oxygen supply and lung volume sensor.

FIG. 40 describes a system schematic of an embodiment of the overall invention, in which the ventilator 20 is powered by compressed air, and bleeds in oxygen from a compressed oxygen supply 200 to deliver a blended supply of air/oxygen to the patient. The compressed air is generated by an internal compressor or external compressed air source, or both. In a preferred embodiment, the oxygen is blended into the ventilator gas delivery circuit 21 from an oxygen concentrator 206 or a source of liquid oxygen 207, which can create oxygen out of the surrounding ambient air. This is useful in situations where access to oxygen deliveries is expensive or logistically complicated. The blender 187 can be inside or outside of the ventilator 20. Because the gas being delivered in the gas delivery circuit 21 is typically being delivered at speeds greater than 50 m/sec, the speed may suck the oxygen into the gas delivery circuit 21 if appropriate valves are used. In an optional embodiment, the system may include an airway gas scavenging system in which some gas from the airway tube is conducted away from the airway tube to an oxygen analyzer 203, a carbon dioxide analyzer 204, or a combined device, which is typically inside of the ventilator 20, and which measures oxygen concentration and/or carbon dioxide concentration. This reading may allow the ventilator 20 or caregiver to know the oxygen concentration in the airway tube that is then correlated to the oxygen concentration in the airways and lung, and, therefore, the FIO2. Pulse oximetry may also be used to establish whether or not the proper air/oxygen mixture is being delivered and what if any adjustment needs to be made. FIG. 40 also shows an optional embodiment in which an impedence breathing volume sensor 209, for example, a thoracic impedance sensor, is used to determine the amount of volume entering the lung during inspiration. The one or more sensors may be controlled by a microprocessor control system 209. In this embodiment, the lung volume information is used to determine the effect of the therapy in the open system, i.e., what is the tidal volume in an open ventilation system. The information can be used to titrate and adjust the parameters, for example increase or decrease the amount of entrainment by adjusting the jet parameters. Tidal volume information can obviate the need for oxygen or carbon dioxide sensors in that if the lung volume and ventilator oxygen volume output is known, then the fractional oxygen concentration in the tidal volume can be calculated.

In the various embodiments of the present invention, the therapy can include a ventilator gas output of 21-100% oxygen. Or, supplemental oxygen gas can be delivered at various alternative locations, and at various points within the breath cycle (inspiration, expiration, cyclically and continuously). The ventilator output can be synchronized with all possible alternatives of the inspiratory cycle, such as early delivered early in inspiration, delivered after a delay, at the middle of inspiration, at the end of inspiration, or overlapping with inspiratory/expiratory phase transition.

Embodiments of the present invention may include various patterns and configurations of fenestrations in the airway tube to allow gas from the airway to also be entrained into the airway tube and out the airway tube distal end toward the lungs. The shape of fenestrations may be circular, oval, or any other reasonable shape, and the fenestrations may be located at any location on the airway tube.

The breathing sensors may be part of the ventilation catheter as is typically shown, or may be part of the airway tube, or maybe inside or outside of the airway, or may be a sensor not associated with the catheter or airway tube. These sensors can measure the patient's respiration pattern for synchronization of the ventilator as desired, and can also measure the entrainment, so the system intelligently knows what the entrainment levels are. This later information can be used to alter the configuration to adjust the source and amplitude of the entrainment. One or more pressure taps may be used to measure gas flow through the airway tube.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

| Reference Symbols | |
|---|---|
| Pt. | Patient |
| T. | Trachea |
| A. | Airway |
| UA. | Upper airway |
| PA. | Oropharyngeal airway |
| L. | Lungs |
| D. | Distal |
| P. | Proximal |
| I. | Inspiratory airflow |
| E. | Expiratory airflow |
| Gv. | Ventilator gas |
| Gsi. | Inspired air through the interface |
| Gsa. | Inspired air through the airway |
| Ge. | Entrained air |

Reference Symbols

| | | |
|---|---|---|
| Gt. | Total inspired gas |
| 1. | Prior art Ventilator |
| 2. | Dual limb gas delivery circuit |
| 3. | Inspiratory limb |
| 4. | Expiratory limb |
| 6. | Endotracheal tube |
| 7. | Endotracheal tube cuff |
| 8. | Prior art Single limb gas delivery circuit |
| 9. | Non-invasive ventilation mask |
| 10. | NIV mask exhaust ports |
| 20. | Ventilator |
| 21. | Single limb gas delivery circuit |
| 23. | Tracheostomy tube |
| 24. | Tracheostomy tube airflow channel |
| 25. | Tracheostomy tube fenestration |
| 26. | Tracheostomy tube cuff |
| 27. | Tracheostomy tube distal tip |
| 29. | Connector Cap |
| 40. | Ventilation catheter |
| 41. | Ventilation catheter nozzle |
| 42. | Airway tube connector |
| 43. | Tracheostomy tube flange |
| 44. | 15 mm connector |
| 45. | Ventilation catheter distal tip |
| 46. | Ventilation gas exit port |
| 47. | Swivel elbow connector |
| 48. | Swivel connector 15 mm female connector |
| 49. | Swivel connector 15 mm male connector |
| 60. | Airway tube |
| 61. | Airway tube flange |
| 62. | Airway tube proximal connector |
| 63. | Airway tube distal end |
| 64. | Baffle connector |
| 65. | Baffle swivel connector |
| 66. | Gas delivery nozzle |
| 80. | Breath sensing line |
| 81. | Airway tube adaptor |
| 82. | Airway tube connector with side connection |
| 83. | Airway tube elbow connector |
| 84. | Airway tube T adaptor |
| 85. | Side connection |
| 86. | Nozzle adjustment slot |
| 87. | Pressure sensing port |
| 89. | Nozzle connection slot |
| 99. | Clip |
| 100. | Low profile connector |
| 101. | Low profile gas delivery nozzle |
| 102. | Heat moisture exchanger |
| 103. | Inspiratory valve |
| 104. | Valve seat |
| 105. | Valve port |
| 106. | Valve diaphragm |
| 107. | Open state |
| 108. | Closed state |
| 109. | Exhalation PEEP valve |
| 120. | Airway sensing extension line |
| 121. | Distal sensing port |
| 122. | Proximal sensing port |
| 123. | Airway tube airway sensing line |
| 124. | Airway tube distal sensing port |
| 125. | Airway tube proximal sensing port |
| 126. | Sensing line connector |
| 127. | Humidification delivery port |
| 128. | Humidification connector |
| 129. | Humidification delivery hose |
| 140. | Humidification catheter |
| 141. | Humidification channel |
| 142. | Humidification reservoir |
| 143. | Breath sensing lumen |
| 144. | Ventilator gas delivery channel |
| 145. | Sensing port facing distally |
| 146. | Sensing port facing proximally |
| 147. | Adaptor swivel |
| 149. | Inline thermal sensor |
| 160. | Thermal sensor wire |
| 161. | Reference thermal sensor |
| 162. | Oxygen delivery port |
| 163. | Oxygen CO2 sensing port |
| 164. | Oxygen delivery lumen |
| 165. | Oxygen CO2 sensing lumen |
| 166. | Inspiratory-Expiratory valve |
| 167. | Exhalation valve seat |
| 168. | Exhalation valve ball |
| 169. | Exhalation valve spring |
| 180. | PEEP PIP relief valve |
| 181. | Valve adjustment |
| 182. | Valve pilot pressure line |
| 183. | Ventilation mask |
| 184. | Mask proximal connector |
| 185. | Mask face seal |
| 186. | Mask strap connection |
| 187. | Blender |
| 188. | External compressor |
| 189. | Compressed air supply |
| 200. | Compressed oxygen supply |
| 201. | Humidifier unit |
| 202. | Internal compressor-turbine |
| 203. | Oxygen analyzer |
| 204. | CO2 analyzer |
| 206. | Oxygen concentrator |
| 207. | Liquid oxygen |
| 208. | Impedance breathing volume sensor |
| 209. | Microprocessor control system |

The invention claimed is:

1. A ventilation system comprising:
a ventilator for supplying ventilation gas;
a patient interface having a generally hollow cylindrical configuration defined by a central lengthwise axis and opposed open ends having substantially equivalent cross-sectional areas and including an open distal end with a distal opening axis coaxial with the central lengthwise axis and being in communication with a patient airway, an opposed open proximal end with a proximal opening axis coaxial with the central lengthwise axis and being in communication with ambient air, and an airflow channel between the distal end and the proximal end;
a gas delivery circuit, wherein the gas delivery circuit is adapted to attach to the patient interface in a coaxial relationship to the proximal opening axis of the open proximal end without occluding the patient interface to allow ambient air to flow from outside the patient interface to the patient airway and to allow patient spontaneous breathing to flow from inside, the patient interface to outside along the central lengthwise axis and the proximal opening axis without obstruction; and
wherein the ventilation gas entrains air from ambient and from the patient airway.

2. The ventilation system of claim 1, wherein the ambient air flows through the patient interface at least during application of the ventilation gas.

3. The ventilation system of claim 1, wherein the patient interface is selected from the group consisting of: an airway tube; a mask; a cannula; and combinations thereof.

4. The ventilation system of claim 1, wherein the ventilator as is delivered in a cycle selected from the group consisting of: as a volume synchronized with the patient's inspiratory cycle, in which the volume is selected by the user; continuously; as a volume delivered cyclically at a rate determined by the ventilator; as a volume cyclically synchronized with the patients breathing, and with a back up rate to deliver a mandatory number of breaths over a period of time; as a volume cyclically during an inspiratory cycle to reduce the work of breathing, and during an expiratory cycle to create PEEP; and combinations thereof.

5. The ventilation system of claim 1, further comprising one or more fenestrations between the distal end and the proximal end of the patient interface, and a nozzle on a distal end of the as delivery circuit, wherein the nozzle is located within the patient interface, and wherein the nozzle is positioned in proximity to the one or more fenestrations when supplying ventilation gas.

6. The ventilation system of claim 5, wherein the ambient air flows through the patient interface at least during application of the ventilation gas.

7. The ventilation system of claim 5, wherein the patient interface is selected from the group consisting of: an airway tube; a mask; a cannula; and combinations thereof.

8. The ventilation system of claim 5, wherein the ventilator gas is delivered in a cycle selected from the group consisting of: as a volume synchronized with the patient's inspiratory cycle, in which the volume is selected by the user; continuously as a volume delivered cyclically at a rate determined by the ventilator as a volume cyclically synchronized with the patients breathing, and with a back up rate to deliver a mandatory number of breaths over a period of time; as a volume Cyclically murine an inspiratory cycle to reduce the work of breathing, and during an expiratory cycle to create PEEP; and combinations thereof.

9. The ventilation system of claim 5, wherein the ventilation system is used to treat a disorder selected from the group consisting of: lung disease; a breathing disorder; a neuromuscular disorder; and combinations thereof.

10. The ventilation system of claim 5, wherein the ventilation system is used with a portable as supply.

11. The ventilation system of claim 5, wherein a distal tip of the gas delivery circuit is a low profile nozzle.

12. The ventilation system of claim 5, wherein a distal tip of the gas delivery circuit is angled to direct the ventilation gas toward an opening at the distal end of the patient interface.

13. The ventilation system of claim 5, wherein the gas delivery circuit is coupled to the patient interface with a baffle connection.

14. The ventilation system o claim 5, further comprising a heat moisture exchanger.

15. The ventilation system of claim 5, wherein the ventilation gas exits the gas delivery circuit distal end as a jet with an exit speed of approximately 50-approximately 350 meters per second.

16. The ventilation system of claim 5, wherein the entrained air is approximately 25-approximately 300% of the ventilation gas.

17. The ventilation system of claim 5, further comprising one or more sensors.

18. The ventilation system of claim 5, wherein humidity is delivered to the patient airway.

19. The ventilation system of claim 5, wherein the ventilation gas is selected from the group consisting of: air, oxygen, helium, NO, HeliOx, and combinations thereof.

20. The ventilation system of claim 5, wherein the ventilator is adapted to vary the gas output parameters to achieve a result selected from the group consisting of: to achieve a desired FI02; to achieve a desired airway pressure; to achieve a desired lung volume: to achieve a desired inspiratory flow rate; and combinations thereof.

21. The ventilation system of claim 5, wherein a distal tip of the gas delivery circuit is approximately 0-1.5 inches from the proximal end of the patient interlace.

22. The ventilation system of claim 5, wherein the gas delivery circuit contacts an inner surface of the patient interface, and a distal tip of the gas delivery circuit is angled to direct the ventilation gas toward the distal end of the patient interface.

23. The ventilation system of claim 5, further comprising one or more pressure taps for measuring flow through the patient interface.

24. The ventilation system of claim 5, further comprising one or more sensors for measuring oxygen concentration, and wherein the ventilation gas is adjusted based upon measurements from the one or more sensors.

25. The ventilation system of claim wherein the ventilation system is used to treat a disorder selected from the group consisting of: lung disease; a breathing disorder; a neuromuscular disorder; and combinations thereof.

26. The ventilation system of claim 1, wherein the ventilation system is used with portable gas supply.

27. The ventilation system of claim 1, wherein a distal end of the gas delivery circuit comprises two gas delivery exit ports, and wherein the patient interface comprises a left and right nasal cannula.

28. The ventilation system of claim 1, wherein a distal tip of the gas delivery circuit is a low profile nozzle.

29. The ventilation system of claim 1, wherein a distal tip of the gas delivery circuit is angled to direct the ventilation gas toward an opening at the distal end of the patient interface.

30. The ventilation system of claim 1, wherein the gas delivery circuit is coupled to the patient interface with a baffle connection.

31. The ventilation system of claim 1, further comprising a heat moisture exchanger.

32. The ventilation system of claim 1, wherein the ventilation gas exits a distal end of the gas delivery circuit as a jet with an exit speed of approximately 50-approximately 350 meters per second.

33. The ventilation system of claim 1, wherein the entrained air is approximately 25-approximately 300% of the ventilation gas.

34. The ventilation system of claim 1, further comprising one or more sensors.

35. The ventilation system of claim 1, wherein humidity is delivered to the patient airway.

36. The ventilation system of claim 1, wherein the ventilation gas is selected from the group consisting of: air, oxygen, helium, NO, HeliOx, and combinations thereof.

37. The ventilation system of claim 1, wherein the ventilator is adapted to vary the gas output parameters to achieve a result selected from the group consisting of: to achieve a desired FI02; to achieve a desired airway pressure; to achieve a desired lung volume to achieve a desired inspiratory flow rate; and combinations thereof.

38. The ventilation system of claim 1, wherein a distal tip of the gas delivery circuit approximately 0-1.5 inches from the proximal end of the patient interface.

39. The ventilation system of claim 1, the gas delivery circuit contacts an inner surface of the patient interface, and a distal tip of the gas delivery circuit is angled to direct the ventilation gas toward the distal end of the patient interface.

40. The ventilation system of claim 1, further comprising one or more pressure taps for measuring flow through the patient interface.

41. The ventilation system of claim 1, further comprising one or more sensors for measuring oxygen concentration, and where in the ventilation gas is adjusted based upon measurements from the one or more sensors.

* * * * *